(12) United States Patent
Krupa et al.

(10) Patent No.: US 10,402,925 B2
(45) Date of Patent: Sep. 3, 2019

(54) EMPLOYEE WELLNESS MANAGEMENT SYSTEM

(71) Applicant: ADP, LLC, Roseland, NJ (US)

(72) Inventors: Wojciech Krupa, Cumming, GA (US); Dariusz Czapla, Cumming, GA (US); Zackary Cully Chapple, Cumming, GA (US)

(73) Assignee: ADP, LLC, Roseland, NJ (US)

( * ) Notice: Subject to any disclaimer, the term of this patent is extended or adjusted under 35 U.S.C. 154(b) by 733 days.

(21) Appl. No.: 14/598,648

(22) Filed: Jan. 16, 2015

(65) Prior Publication Data
US 2016/0210711 A1 Jul. 21, 2016

(51) Int. Cl.
*G06Q 50/22* (2018.01)
*G06Q 10/06* (2012.01)
*G06Q 10/10* (2012.01)

(52) U.S. Cl.
CPC .......... *G06Q 50/22* (2013.01); *G06Q 10/06* (2013.01); *G06Q 10/1057* (2013.01)

(58) Field of Classification Search
CPC ..... G06Q 50/22; G06Q 10/06; G06Q 10/1057
See application file for complete search history.

(56) References Cited

U.S. PATENT DOCUMENTS

| 8,359,208 | B2 * | 1/2013 | Slutzky | .................. | G06F 19/328 |
| | | | | | 705/2 |
| 2007/0136102 | A1 * | 6/2007 | Rodgers | ................ | A61B 5/1113 |
| | | | | | 705/3 |
| 2008/0319858 | A1 * | 12/2008 | Denk, Jr. | ............ | G06F 17/3089 |
| | | | | | 705/14.13 |
| 2009/0269728 | A1 * | 10/2009 | Verstegen | ........ | A63B 21/00196 |
| | | | | | 434/247 |
| 2010/0332259 | A1 * | 12/2010 | Condon | ................. | G06Q 40/08 |
| | | | | | 705/3 |
| 2011/0288876 | A1 | 11/2011 | Cardillo et al. | | |
| 2013/0103672 | A1 | 4/2013 | Parikh et al. | | |

(Continued)

FOREIGN PATENT DOCUMENTS

| WO | WO2009143525 A2 | 11/2009 |
| WO | WO2010002947 A2 | 1/2010 |
| WO | WO2012090226 A2 | 7/2012 |

OTHER PUBLICATIONS

Centers for Disease Control and Prevention, "School Health Guidelines to Promote Healthy Eating and Physical Activity," Morbidity and Mortality Weekly Report Recommendations and Reports, vol. 60, No. 5, Sep. 2011, 80 pages. http://www.cdc.gov/mmwr/preview/mmwrhtml/rr6005a1.htm.

(Continued)

*Primary Examiner* — Victoria P Augustine
*Assistant Examiner* — Chad A Newton
(74) *Attorney, Agent, or Firm* — Yee & Associates, P.C.

(57) ABSTRACT

A method managing wellness of employees is presented. A computer system receives a group of health factors for activities and group of preferences for activities of the employees. The computer system identifies a recommendation for an activity for a portion of the employees based on the group health factors, the group of preferences, and information for locations where recommended activities are to occur. The computer system then sends the recommendation for the activity to the portion of the employees.

36 Claims, 25 Drawing Sheets

(56) References Cited

U.S. PATENT DOCUMENTS

| | | | | |
|---|---|---|---|---|
| 2013/0275511 A1* | 10/2013 | Wilson | ................... | G06N 3/02 |
| | | | | 709/204 |
| 2014/0255882 A1* | 9/2014 | Hadad | ................ | G09B 19/0092 |
| | | | | 434/127 |
| 2014/0343991 A1* | 11/2014 | Hofstee | .............. | G06Q 30/0601 |
| | | | | 705/7.18 |
| 2015/0134731 A1 | 5/2015 | Wang et al. | | |
| 2016/0151674 A1* | 6/2016 | Rauhala | ................... | G09B 5/04 |
| | | | | 434/247 |
| 2016/0210568 A1 | 7/2016 | Krupa et al. | | |

OTHER PUBLICATIONS

Krupa et al., "Employee Preference Identification in a Wellness Management System," U.S. Appl. No. 14/598,706, filed Jan. 16, 2015, 92 pages.

Office Action, dated Feb. 8, 2018, regarding U.S. Appl. No. 14/598,706, 35 pages.

Final Office Action, dated Aug. 28, 2018, regarding U.S. Appl. No. 14/598,706, 30 pages.

* cited by examiner

FIG. 2

Current Activity

Quick Walk
As part of our effort to raise money for breast cancer awareness we are going to walk around the office.

204 — Rankings By: (Steps) (Distance) (Calories)
Business Development
IT
Exec Prod Management
Exec IT Welcome Wojciech Krupa!
Go to admin — 202
1529 / 10000 Steps
15% of your daily step goal.
14% of your daily distance goal.

⚙ Log out

Steps 206
50k
25k
0k
7-Dec, 8-Dec, 9-Dec, 10-Dec, 11-Dec, 12-Dec, 13-Dec, 14-Dec

Breast Cancer Awareness Month 🎗
210
Steps: 75861 / 100000
Funds Raised: $8512 / $10000
Distance: 25 / 30 Miles ♟ Ranking (Steps) (Distance) (Calories)
- Eric Liu — 2343
- Wojciech Krupa — 1529
- Dariusz Czapla — 305
- Zach Chapple — 0
- Paul Gourley — 0
- Jimmy Adams — 0

208

Flag Football (Just Finished!)
ADP Courtyard
A day of fun! Make sure to lay it all out on the field!

Feedback 👍 20    Attendance 25 / 38

Disc Golf (Up Next)
Fowler Park
Nice relaxing game of golf!

Who's Going
😊 25 / ☹ 0 / Maybe? 2

216

News Feed
- ← Dariusz passed Jimmy
  There is still time to catch up Jimmy!
- ← Dariusz passed Paul
  There is still time to catch up Paul!
- ← Dariusz passed Zack
  There is still time to catch up Zack!
- ← Dariusz passed Wojciech
  There is still time to catch up Wojciech!
- ← Eric passed Jimmy
  There is still time to catch up Jimmy!
- ← Eric passed Paul
  There is still time to catch up Paul!

212
214

200

EMPLOYEE WELLNESS MANAGEMENT SYSTEM

CROSS REFERENCE TO RELATED APPLICATION(S)

This application is related to co-pending U.S. patent application Ser. No. 14/598,706, entitled "Employee Preference Identification in a Wellness Management System", filed concurrently herewith on Jan. 16, 2015, which is incorporated by reference herein in its entirety.

BACKGROUND INFORMATION

1. Field

The present disclosure relates generally to an improved data processing system. In particular, the present disclosure relates to a method and apparatus for managing the wellness of employees in an organization. Still more particularly, the present disclosure relates to a method and apparatus for a graphical user interface used in recommending and scheduling activities to employees of an organization to facilitate a desired level of wellness.

2. Background

Information systems are used for many different purposes. For example, an information system may be used to process payroll to generate paychecks for employees in an organization. Additionally, an information system also may be used by a human resources department to maintain benefits and other records about employees. For example, a human resources department may manage health insurance, wellness plans, and other programs and organizations using an employee information system.

Current systems implementing employee wellness plans include fitness goals and activity rewards for monitored employees. However, these employee systems plans lack capabilities to encourage and maximize employee participation based on scheduling activities that are specifically interesting to the employee. As a result, current employee wellness systems are often underutilized or completely disregarded by employees.

Therefore, it would be desirable to have a method and apparatus that take into account at least some of the issues discussed above, as well as other possible issues. For example, it would be desirable to have a method and apparatus that overcome issues with employee wellness systems that are underutilized by nonparticipating employees.

SUMMARY

In one illustrative embodiment, a method for managing wellness of employees is presented. A computer system receives a group of health factors for activities and group of preferences for activities of the employees. The computer system identifies a recommendation for an activity for a portion of the employees based on the group health factors, the group of preferences, and information for locations where recommended activities are to occur. The computer system then sends the recommendation for the activity to the portion of the employees.

In another illustrative embodiment, a computer system comprises a wellness management system for managing wellness of employees. The wellness management system receives a group of health factors for activities and group of preferences for activities of the employees. The wellness management system identifies a recommendation for an activity for a portion of the employees based on the group health factors, the group of preferences, and information for locations where recommended activities are to occur. The wellness management system then sends the recommendation for the activity to the portion of the employees.

In yet another illustrative embodiment, a computer program product for managing wellness of employees comprises a computer readable storage media, and program code stored on the computer readable storage media. The program code instructs wellness management system to receive a group of health factors for activities and group of preferences for activities of the employees. The program code instructs the wellness management system to identify a recommendation for an activity for a portion of the employees based on the group health factors, the group of preferences, and information for locations where recommended activities are to occur. The program code then constructs the wellness management system to send you the recommendation for the activity to the portion of the employees.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 2 is an illustration of a graphical user interface for employee interaction with a wellness management system depicted in accordance with an illustrative embodiment;

DETAILED DESCRIPTION

Figure 1:
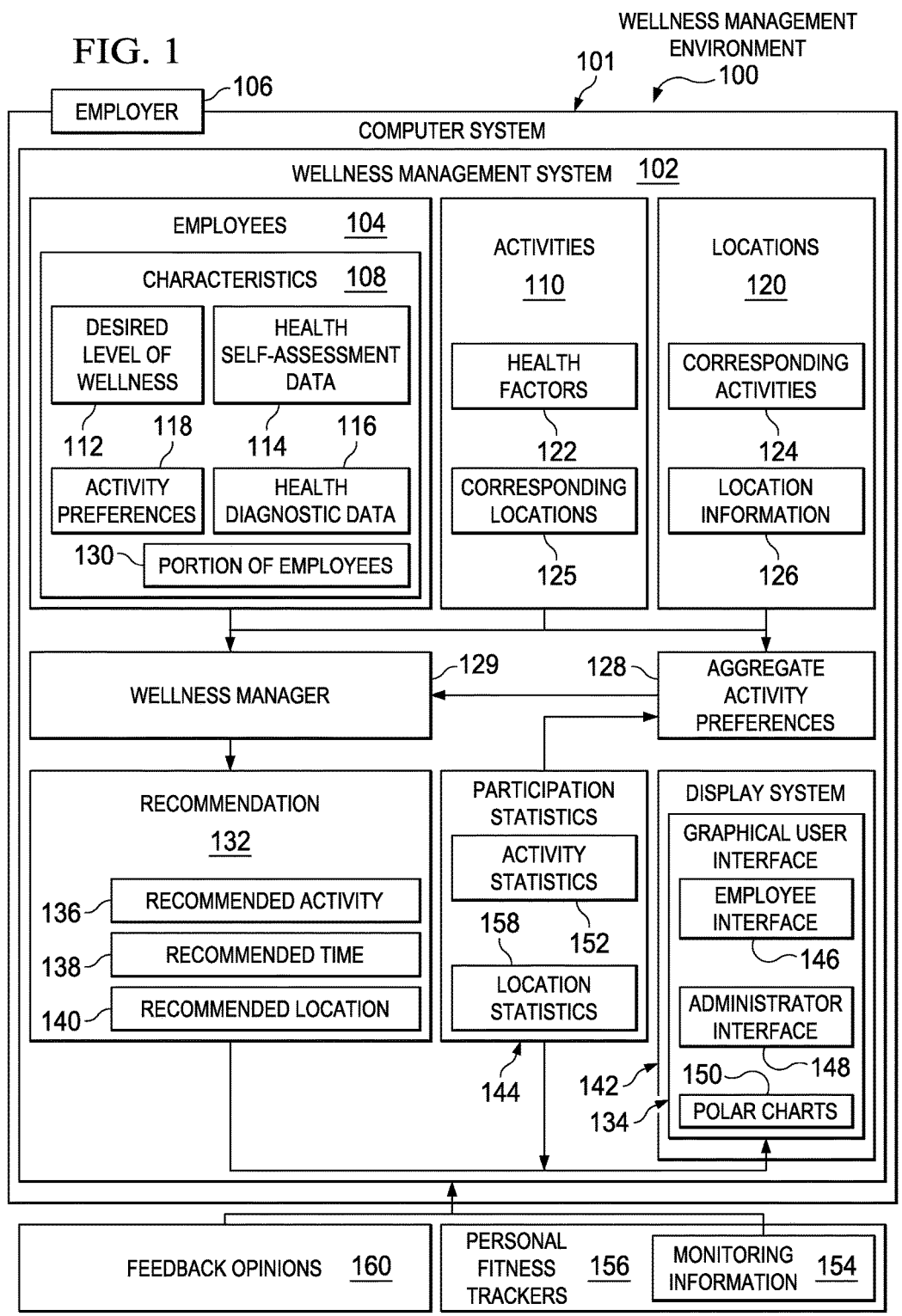
FIG. 1 is a block diagram of a wellness management environment depicted in accordance with an illustrative embodiment.

The illustrative embodiments recognize and take into account one or more different considerations. For example, the illustrative embodiments recognize and take into account that the concept of managing employee wellness may be viewed as a method of organizing human actions that is based on the fundamental building blocks of gathering employee wellness information, analyzing employee wellness information, and taking appropriate action to manage the wellness of employees on the analysis of the employee wellness information. The different illustrative embodiments recognize and take into account that current systems and methods of managing employee wellness may be limited in various ways. The illustrative embodiments implement and integrate the basic building blocks of managing employee wellness into something significantly more by applying the basic building blocks in a meaningful way to improve managing employee wellness beyond that provided by current uses of these basic building blocks. For example, the illustrative embodiments expand upon and integrate the basic building blocks of managing employee wellness into something significantly more by enabling a personalized approach to recommending, scheduling, monitoring, and evaluating activities to be performed as part of an employee wellness management system.

For example, the illustrative embodiments recognize and take into account that in scheduling activities within an employee wellness management system, various characteristics about the employees, the activities, and locations at which the activities take place may be used to increase a likelihood of employee participation in those activities. Characteristics of the employee may include, for example, an employee's desired level of wellness, an employee's health self-assessment data, an employee's health diagnostic data, and an employee's activity preferences. Characteristics of the activity may include activity health factors. Characteristics of the location may include location information.

The illustrative embodiments recognize and take into account that scheduling activities within an employee wellness management system that appeal to a broad range of employees may be more difficult to compare than desired. The illustrative embodiments also recognize and take into account that encouraging participation in scheduled activities of an employee wellness management system may be more difficult than desired.

Thus, the illustrative embodiments provide a method and apparatus recommending, scheduling, monitoring, and evaluating activities to be performed as part of an employee wellness management system. These recommended activities are for people in an organization. In particular, the people may be employees in an organization. In one example, a process for managing wellness of employees is presented. The process receives, by a computer system, a group of health factors for activities and group of preferences for activities of the employees. The process identifies, by the computer system, a recommendation for an activity for a portion of the employees based on the group health factors, the group of preferences, and information for locations where recommended activities are to occur. The process then sends, by the computer system, the recommendation for the activity to the portion of the employees.

With reference now to the figures and in particular with reference to FIG. 1, an illustration of a block diagram of a wellness management environment is depicted in accordance with an illustrative embodiment. Wellness management environment 100 includes wellness management system 102. Wellness management system 102 is used to perform operations with respect to employees 104. The operations can be, for example but not limited to, at least one of recommending, scheduling, monitoring, and evaluating activities to be performed by employees 104. As depicted, employees 104 are people who are employed by or associated with an entity for which wellness management system 102 is implemented, such as employer 106.

Wellness management system 102 can be implemented in computer system 101, where the computer system is a hardware system includes one or more data processing systems. When more than one data processing system is present, those data processing systems may be in communication with each other using a communications medium. The communications medium may be a network. The data processing systems may be selected from at least one of a computer, a workstation, a server computer, a tablet computer, a laptop computer, a mobile phone, a personal digital assistant (PDA), or some other suitable data processing system.—then we can say that the steps may be distributed to different data processing systems in the computer system—then we have a data processing system diagram that shows a processor unit—that has one or more processors—i.e. chips with one or more cores on each chip.

Associated with each of employees 104 are characteristics 108. Characteristics 108 are tracked information about the associated one of the employees 104 that can be used to schedule activities 110 for managing the wellness of employees 104. Characteristics 108 can include at least one of desired level of wellness 112, health self-assessment data 114, health diagnostic data 116, activity preferences 118, or other suitable characteristics.

As used herein, the phrase "at least one of," when used with a list of items, means different combinations of one or more of the listed items may be used and only one of each item in the list may be needed. In other words, at least one of means any combination of items and number of items may be used from the list but not all of the items in the list are required. The item may be a particular object, thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

Characteristics 108 can include desired level of wellness 112. Desired level of wellness 112 can be at least one of a target standard or goal for various health related parameters. Desired level of wellness 112 set by at least one of employees 104 or employer 106, and can include, for example but not limited to, standards or goals for at least one of blood pressure, cholesterol, triglycerides, glucose, or body mass index for employees 104. Desired level of wellness 112 can include, for example but not limited to, standards or goals for a duration of activities to be performed, or an intensity of activities to be performed, which can be measured for example by an amount of energy expenditure of the employees 104 or rate of energy expenditure of the employees 104. Desired level of wellness 112 can include one-time standards or goals, or also periodic repeating standards or goals, such as daily goals, weekly goals, yearly goals, or some other suitable types of goals.

Desired level of wellness 112 can include, for example but not limited to, standards or goals for each of the employees 104 individually, as well as standards or goals for employees 104 in the aggregate. When aggregated, employer 106 can use desired level of wellness 112 to negotiate health insurance premiums or coverage or healthcare premiums or coverage from a healthcare or insurance provider. This negotiation can be based on identifying a lower cost for the health insurance or have healthcare resulting from attaining the standards or goals by employees 104 individually or in the aggregate. In this manner, each of employees 104 is incentivized to perform activities in order to attain desired level of wellness 112.

Characteristics 108 can include health self-assessment data 114. Health self-assessment data 114 is a qualitative measure of various health characteristics as provided by employees 104. Health self-assessment data 114 can include, for example but not limited to, an employee's self-evaluation of at least one of health, allergies, nutrition, stress, tobacco use, alcohol use, sleep habits, or other suitable metrics for health self-assessment data 114.

Characteristics 108 can include health diagnostic data 116. Health diagnostic data 116 is a quantitative measure of various health characteristics of employees 104. Health diagnostic data 116 can include, for example but not limited to, measurement at least one of blood pressure, cholesterol, triglycerides, glucose, or body mass index, or some other type of data for an employee.

Characteristics 108 can include activity preferences 118. Activity preferences 118 are indications from each of employees 104 as to the type or nature of activities typically enjoyed by the employee, or in which activities the employee is likely to participate.

Activity preferences 118 can include an indication of a specific activity. The specific activity may include, for example but not limited to, at least one of a soccer, football, yoga, frisbee, walking, basketball, tennis, table tennis, biking, skiing, weightlifting, hiking, or some other suitable activity.

Activity preferences 118 can include an indication of a general activity. The general activity may include, for example but not limited to, outdoor activities, indoor activities, team activities, individual activities, activities having a certain level of social interaction, activities likely to burn a desired number of calories, activities having a desired physical intensity level of the activities, activities occurring at a particular location, or activities occurring at a location having particular location, or some other suitable preference. The location can be, for example, one of locations 120, as discussed below.

Activity preferences 118 can be updated based on feedback received from employees 104 upon the completion of an activity. For example, if one of employees 104 indicates a positive or negative opinion of a particular one of activities 110, that employee's activity preferences 118 can be updated to reflect the indication. Similarly, if one of employees 104 indicates a positive or negative opinion of a particular location, that employee's activity preferences 118 can be updated to reflect the indication. Feedback for a particular location can also be used to update location information 126, as discussed below.

Activities 110 is a listing of physical activities, actions, or exercises that wellness management system 102 can recommend to employees 104. Activities 110 may include, for example but not limited to specific activities, such as at least one of a soccer, football, yoga, frisbee, walking, basketball, tennis, table tennis, biking, skiing, weightlifting, hiking, or some other suitable activity.

Each of activities 110 include health factors 122. Health factors 122 are characteristics of the associated one of activities 110. Health factors 122 may indicate, for example but not limited to, that the associated one of activities 110 is one or more of an outdoor activity, and indoor activity, a team activity, or an individual activity. Additionally, health factors 122 may indicate, for example but not limited to, that the associated one of activities 110 is associated with a certain level of social interaction, is likely to burn a certain number of calories, is associated with a particular intensity level, has achieved a certain popularity among employees 104, or some other suitable health factor.

Locations 120 is a listing of various geographical locations, venues, recreational areas, or other locations at which at least one of activities 110 can occur. For example, locations 120 may include, but are not limited to at least one of a park, a swimming pool, an office building, a recreational area, a recreational sports arena, a recreational sports facility, or other location.

Each of locations 120 includes a listing of corresponding activities 124. Corresponding activities 124 are activities 110 that can occur on facilities at the associated one of locations 120. For example, locations 120 may include several recreational areas. However, recommendations for tennis should be scheduled only at ones of those recreational areas where tennis courts are located. Each of locations 120 may be associated with at least one of, or more than one corresponding activities 124. Similarly, each of activities 110 may be associated with at least one of, or more than one of corresponding locations 125.

Each of locations 120 include location information 126. Location information 126 is characteristics of the associated location. Location information 126 can include, for example but not limited to, at least one of a popularity of the location, expected weather conditions during a time when a particular activity is to occur, safety conditions of the location, whether the location is a recommended location, whether the location is preferred location, or whether the location carries insurance or coinsurance on a particular activity.

Location information 126 can include a popularity of the location. Popularity of a location is an aggregated positive or negative opinion of employees 104 regarding the associated one of locations 120. Popularity of a location can be updated based on feedback received from employees 104 upon the completion of an activity occurring at that location. When a particular location attains a certain level of popularity by receiving a certain level of positive feedback, that location can be indicated as a recommended location.

Location information 126 can include expected weather conditions. Expected weather conditions is a forecast of projected conditions occurring at locations 120. Expected weather conditions can include atmospheric conditions, such as but not limited to, at least one of a forecast the temperature a forecasted chance of precipitation, or some other suitable weather condition. Expected weather conditions can also include expected allergy conditions, such as but not limited to, at least one of forecasted pollen levels, forecasted mold levels, forecasted dust levels, forecasted ozone levels, or some other suitable allergy condition.

Location information 126 can include safety conditions. Safety conditions are unsafe conditions present at a location that can potentially cause injury, illness or death. Safety conditions of the location can include, for example but not limited to, unsanitary conditions, unsafe equipment, lack of adequate safety equipment, lack of adequate supervision, potential trip hazards, potential fall hazards, or other conditions present at the location that can potentially cause injury, illness, or death. Safety conditions of a location can be updated based on feedback received from employees 104 upon the completion of an activity occurring at that location. When a particular location receiving a certain level of positive feedback regarding safety conditions at that location, that location can be indicated as a preferred location. Additionally, whether the location carries insurance or co-insurance on particular activities to occur can also factor into whether that location is indicated as a preferred location.

Based on characteristics 108 of employees 104 and activities 110, wellness management system 102 can determine aggregate activity preferences 128. Aggregate activity preferences 128 can be statistical calculations, statistical weights, or other values that indicate an aggregated opinion of employees 104 about activities 110.

Aggregate activity preferences 128 can include a statistically based indication of ones of activities 110 that are preferentially enjoyed by employees 104, or a statistically significant portion thereof. Similarly, aggregate activity preferences 128 can include a statistically based indication of ones of activities 110 in which a statistically significant portion of employees 130 is likely to participate. As used herein, statistically significant can be at least one of a percentage of employees 104, a finite number of employees 104, or a requisite number of employees 104 needed to participate in an activity.

Aggregate activity preferences 128 can include an indication of a general activity enjoyed by employees 104, or a statistically significant portion thereof. Aggregate activity preferences 128 can include an indication of a general activity in which a statistically significant portion of employees 104 is likely to participate. Aggregate activity preferences 128 can include statistically aggregated opinions regarding locations 120, or health factors 122.

Aggregate activity preferences 128 can be updated based on updates to activity preferences 118. According to an illustrative embodiment, aggregate activity preferences 128 can be utilized in determining recommended locations and preferred locations. Based on aggregate activity preferences 128, activities 110, and locations 120, wellness manager 129 in wellness management system 102 can make recommendation 132.

Wellness manager 129 may be implemented in software, hardware, firmware or a combination thereof. When software is used, the operations performed by wellness manager 129 may be implemented in program code configured to run on hardware, such as a processor unit. When firmware is used, the operations performed by wellness manager 129 may be implemented in program code and data and stored in persistent memory to run on a processor unit. When hardware is employed, the hardware may include circuits that operate to perform the operations in wellness manager 129.

In the illustrative examples, the hardware may take the form of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components excluding a human being. For example, the processes may be implemented as circuits in organic semiconductors.

Recommendation 132 can be a recommendation to employees 104 or portion of employees 130 for the scheduling of one of activities 110. Recommendation 132 can take the form of, for example but not limited to, at least one of an icon or graphic within a graphical user interface, an e-mail, a chat message, or a short messaging service (SMS) message. In one illustrative embodiment, a recommendation 132 is an interactive icon or graphic displayed within a graphical user interface, such as graphical user interface 134, as discussed below.

Recommendation 132 can be a recommendation to employees 104 or portion of employees 130 for the scheduling of one of activities 110. Portion of employees 130 can be ones of employees 104 having at least one of a common desired level of wellness 112, common health self-assessment data 114, common health diagnostic data 116, or common activity preferences 118. In this manner, recommendation 132 can be sent to portion of employees 130 that share at least one of common fitness goals, common present fitness levels, or common interests in recommended activity 136. Portion of employees 130 is therefore more likely to participate in recommended activity 136.

Alternatively, portion of employees 130 can be one of a user selected subgroup of employees 104 or an administrator selected subgroup of employees 104. In this manner, recommendation 132 can be sent to portion of employees 130 that, for example, share a common social circle, share a common department, share a common managerial level, or share a common workgroup, and are therefore more likely to participate in recommended activity 136.

Recommended activity 136 is one of activities 110 that is recommended to portion of employees 130. Wellness manager 129 can identify recommended activity 136 from aggregate activity preferences 128.

In one illustrative embodiment, wellness manager 129 can preferentially identify recommended activity 136 when recommended activity 136 or has achieved a certain popularity among employees 104, or when portion of employees 130 indicating a preference for recommended activity 136 is a statistically significant portion of employees 104.

Recommended time 138 is a time at which or during which recommended activity 136 occurs. According to an illustrative embodiment, wellness management system 102 can identify recommended time 138 based on availability information parsed from calendar applications for employees 104. In this manner, wellness management system 102 can account for scheduled vacation days, personal days, sick days, times during which business activities or meetings are scheduled for employees 104, times during which employees 104 are geographically remote from recommended location 140, times during which others of activities 110 are scheduled for employees 104, or other conflicting engagements that might impede employees 104 or portion of employees 130 from participating in recommended activity 136.

According to one illustrative embodiment, once recommended time 138 is identified, wellness management system 102 can modify portion of employees 130 to include others of employees 104 based on calendared events for those other employees. For example, wellness management system 102 may identify employees 104 that do not have other scheduled events during recommended time 138. Wellness manager 129 can send recommendation 132 to portion of employees 130, and additionally send recommendation 132 to those other employees in order to, for example, introduce those other employees to additional activities, introduce those other employees to portion of employees 130, or to facilitate the other employees attaining desired level of wellness 112.

Recommended location 140 is one of locations 120 at which recommended activity 136 occurs at recommended time 138. According to an illustrative embodiment, wellness management system 102 can identify recommended location 140 based on the location information 126, activity preferences 118, and whether recommended activity 136 is a corresponding activity 124 recommended location 140.

Recommended location 140 takes into account location information 126. Therefore, recommendation 132 can be tailored to the specific conditions present at recommended location 140. Because recommended location 140 also takes into account aggregate activity preferences 128, recommendation 132 can be tailored to opinions of employees 104 or portion of employees 130 regarding recommended location 140. Therefore, wellness management system 102 can identify recommended location 140 in a manner that is likely to increase participation in recommended activity 136 and achieve desired level of wellness 112 for portion of employees 130.

As depicted, wellness management system 102 includes display system 142. In this illustrative example, display system 142 can be a group of display devices. A display device in display system 142 may be selected from one of a liquid crystal display (LCD), a light emitting diode (LED) display, an organic light emitting diode (OLED) display, and other suitable types of display devices.

In this illustrative example, display system 142 includes graphical user interface 134. In this illustrative example, wellness management system 102 can display information such as for example, at least one of user identification, current activities, historic monitoring information, employee wellness rankings, employer-sponsored incentives, employer-sponsored campaigns, recommendation 132, participation statistics 144, or other suitable information in graphical user interface 134.

Wellness management system 102 may receive user input selecting the display information in graphical user interface 134. Wellness management system 102 may also receive user input through graphical user interface 134 recommending, scheduling, monitoring and analyzing various activities 110 to be performed by employees 104, or a portion of employees 130, at one of locations 120.

In this illustrative example, graphical user interface 134 includes employee interface 146. Employee interface 146 is an interface through which employees 104 can interact with wellness management system 102. Wellness management system 102 can display, for example at least one of user identification, current activities, employee historic monitoring information, employee wellness rankings, employer-sponsored incentives, employer-sponsored campaigns, real-time wellness information, recommendation 132, participation statistics 144, or other suitable information in employee interface 146. Through employee interface 146, employees 104 can indicate desired level of wellness 112, health self-assessment data 114, health diagnostic data 116, and activity preferences 118.

In this illustrative example, graphical user interface 134 includes administrator interface 148. Administrator interface 148 is an interface through which the administrators of wellness management system 102 or designated ones of employees 104 can interact with wellness management system 102. Wellness management system 102 can display information such as, for example at least one of administrator identification, current activities, employee historic monitoring information, employee wellness rankings, employer-sponsored incentives, employer-sponsored campaigns, real-time wellness information, aggregated wellness information, aggregate activity preferences 128, recommendation 132, participation statistics 144, or other suitable information in administrator interface 148.

Administrator interface 148 is an interface through which administrators of wellness management system 102 or designated ones of employees 104 can receive input for recommending, scheduling, monitoring and analyzing various activities 110 to be performed by employees 104, or a portion of employees 130, at one of locations 120.

In this illustrative example, graphical user interface 134 can display at least one of aggregate activity preferences 128 or participation statistics 144 in polar charts 150. Polar charts 150 are graphical displays of aggregate activity preferences 128 or participation statistics 144 in the form of a two-dimensional chart represented on axes starting from the same point. The data length of an axes is proportional to the magnitude of the aggregate activity preferences 128 or participation statistics 144 for an associated one of activities 110 relative to a maximum magnitude of one of aggregate activity preferences 128 or one of participation statistics 144 across all other activities 110 displayed in polar charts 150. A line is drawn connecting the data values for each spoke.

By displaying the information in polar charts 150, wellness management system 102, administrators utilizing administrator interface 148 can more quickly determine at least one of normalities, similarities, or outliers among employees 104, activities 110, locations 120, aggregate activity preferences 128, and participation statistics 144.

By locating similar or dissimilar ones of activities 110, locations 120, aggregate activity preferences 128, and participation statistics 144 within polar charts 150, wellness management system 102 can preferentially make recommendation 132 for activities and locations preferred by employees 104 or portion of employees 130 in order to maximize participation of portion of employees 130 in recommendation 132. Similarly, wellness management system 102 can preferentially not make recommendation 132 for activities and locations not preferred by employees 104 or portion of employees 130.

By locating similar or dissimilar ones of activities 110, locations 120, aggregate activity preferences 128, and participation statistics 144 within polar charts 150, wellness management system 102 can make recommendation 132 for ones of activities 110 and locations 120 that are similar to, but not necessarily indicated by, activity preferences 118 for a particular one of employees 104.

By locating outliers among activities 110, locations 120, aggregate activity preferences 128, and participation statistics 144 within polar charts 150, wellness management system 102 can identify at least one of health factors 122 or location information 126 that contributes to an uncharacteristic popularity or unpopularity of the one of activities 110 or one of locations 120. Wellness management system 102 can then make recommendation 132, giving preference for activities 110 and locations 120 that share the uncharacteristically popular health factors 122 or location information 126. Wellness management system 102 can make recommendation 132, negatively weighting activities 110 and locations 120 that do not share the uncharacteristically popular health factors 122 or location information 126.

In this manner, the display of activities 110, locations 120, aggregate activity preferences 128, and participation statistics 144 within polar charts 150 can help to maximize participation of portion of employees 130 in recommended activity 136. By maximizing participation of employees 104, wellness management system 102 can facilitate portion of employees 130 in attaining desired level of wellness 112.

Participation statistics 144 includes activity statistics 152. Activity statistics 152 are statistical information describing participation of employees 104 or portion of employees 130, in recommended activity 136. Activity statistics 152 can include registration statistics such as but not limited to, at least one of a number of employees 104 registering for recommended activity 136, a percentage of employees 104 registering for recommended activity 136, a number of portion of employees 130 registering for recommended activity 136, or a percentage of portion of employees 130 registering for recommended activity 136. Registration statistics can be monitored based on interactions of employees 104 with employee interface 146, indicating an intention to participate in recommended activity 136.

Activity statistics 152 can include participation statistics such as but not limited to, at least one of a number of employees 104 participating in recommended activity 136, a percentage of employees 104 participating in recommended activity 136, a number of portion of employees 130 participating in recommended activity 136, a percentage of portion of employees 130 participating in recommended activity 136, a number employees 104 who registered for and participated in recommended activity 136, a percentage of employees 104 who registered for and participated in recommended activity 136, a number portion of employees 130 who registered for and participated in recommended activity 136, or a percentage of portion of employees 130 who registered for and participated in recommended activity 136. Participation statistics can be monitored based on wellness management system 102 receiving monitoring information 154 from personal fitness trackers 156 discussed below, indicating an associated one of employees 104 actually participated in recommended activity 136.

Activity statistics 152 can include other statistics based on monitoring information 154 received from personal fitness trackers 156. For example, activity statistics 152 can include statistics related to an activity level of recommended activity 136, such as a number of calories burned. Activity statistics 152 can include statistics related to biometric data during participation recommended activity 136. For example, activity statistics 152 may include as a heart rate, a respiratory rate, blood pressure, or other biometric data collected by personal fitness trackers 156 during performance of recommended activity 136.

Activity statistics 152 can also include opinion statistics regarding the opinions of employees 104 participating in recommended activity 136. The opinions can be received as feedback opinions 160 received through employee interface 146. Feedback opinions 160 can include opinions about recommended activity 136, such as for example but not limited to, at least one of opinions about the recommended activity 136, whether recommended activity 136 was enjoyable, a likelihood to participate in identical recommended activities, or a likelihood to participate in similar recommended activities.

Participation statistics 144 includes location statistics 158. Location statistics 158 are statistical information regarding recommended location 140 during recommended time 138. Location statistics 158 can include statistics related to location information 126.

Location statistics 158 can include monitored weather statistics, such as but not limited to, at least one of a measured temperature at recommended time 138 or measured precipitation at recommended time 138. Monitored weather statistics can also include measured allergy conditions at recommended location 140 during recommended time 138, such as but not limited to, at least one of measured pollen levels, measured mold levels, measured dust levels, or measured ozone levels. Monitored weather statistics can be recorded as monitoring information 154 by personal fitness trackers 156, and transferred to wellness management system 102 during synchronization with personal fitness trackers 156.

Location statistics 158 can also include opinion statistics regarding the opinions of employees 104 participating in recommended activity 136. The opinions can be received as feedback opinions 160 received through employee interface 146. Feedback opinions 160 can include opinions about recommended location 140, such as for example but not limited to, at least one of opinions about the weather at recommended location 140 during recommended activity 136, opinions about a safety of recommended location 140 during recommended activity 136, opinions about a security of recommended location 140 during recommended activity 136, a likelihood to participate in identical recommended activities at recommended location 140, or a likelihood to participate in similar recommended activities at recommended location 140.

Personal fitness trackers 156 are wearable technology devices for monitoring and tracking fitness-related metrics of employees 104. Personal fitness trackers 156 collect monitoring information 154 during the performance of recommended activities 136.

Personal fitness trackers 156 can be synchronized with wellness management system 102 for transfer of monitoring information 154. Wellness management system 102 can then correlate monitoring information 154 to recommended activity 136. Wellness management system 102 can then update activity preferences 118, health factors 122, location information 126, aggregate activity preferences 128, and participation statistics 144 based on correlating monitoring information 154 to recommended activity 136.

Personal fitness trackers 156 can be heterogeneous personal fitness trackers. In this manner, each of employees 104 are not restricted to a particular make or model of personal fitness tracker 156.

According to one illustrative embodiment, personal fitness tracker 156 includes a location monitoring system, such as a global positioning system. The location of the personal fitness tracker 156 is recorded in monitoring information 154. Wellness management system 102 compares recorded locations in monitoring information 154 with location information 126 of locations 120. If the recorded location of personal fitness tracker 156 correlates to one of recommended locations 140 during recommended time 138, wellness management system 102 assumes that an associated one of employees 104 participated in recommended activity 136.

Personal fitness tracker 156 records monitoring information 154 at least during the performance of recommended activity 136. Monitoring information 154 can include various fitness related metrics, such as but not limited to, at least one of a number of steps taken during recommended activity 136, a number of calories burned during recommended activity 136, a distance traveled during recommended activity 136, an exercise duration of recommended activity 136, a heart rate during recommended activity 136, a respiratory rate during recommended activity 136, a blood pressure during recommended activity 136, or other suitable biometric data that can be collected by personal fitness trackers 156.

In the illustrative example, wellness management system 102 may be used to recommend, schedule, monitor and analyze various activities 110 to be performed by employees 104, or a portion of employees 130, at one of locations 120. By recommending, scheduling, monitoring, and analyzing activities performed by employees 104, Wellness management system 102 can enable a desired level of wellness among employees 104.

When aggregated, employer 106 can use desired level of wellness 112 to negotiate health insurance premiums or coverage or healthcare premiums or coverage from a healthcare or insurance provider. This negotiation can be based on identifying a lower cost for the health insurance or have healthcare resulting from attaining the standards or goals by employees 104 individually or in the aggregate.

As a result, computer system 101 operates as a special purpose computer system in which wellness manager 129 in computer system 101 enables recommending, scheduling, monitoring, and evaluating activities to be performed as part of an employee wellness management system based on activity health factors and activity preferences. Wellness manager 129 identifies a recommendation for an activity for a portion of the employees based on the group health factors, the group of preferences, and information for locations where recommended activities are to occur. Wellness manager 129 enables personalization of recommended activities by identifying an employee's health factors and preferences.

Wellness manager 129 enables a personalized approach to recommending, scheduling, monitoring, and evaluating activities to be performed as part of an employee wellness management system. Thus, wellness manager 129 transforms computer system 101 into a special purpose computer system as compared to currently available general computer systems that do not have wellness manager 129.

The illustration of wellness management system 102 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, wellness manager 129 may be used to track employee activities as part of a calendar system. As another illustrative example, changes to employee preferences can be displayed and manipulated for single employees as well as groups of employees.

With reference next to FIG. 2, an illustration of a graphical user interface for employee interaction with a wellness management system is depicted in accordance with an illustrative embodiment. As depicted, employee interface 200 is an example of employee interface 146 of graphical user interface 134 in FIG. 1.

As depicted, employee interface 200 can display at least one of employee identification 202, current activities 204, employee historic monitoring information 206, employee wellness rankings 208, employer-sponsored campaigns 210, real-time wellness information 212, previous recommendation 214 and upcoming recommendation 216.

Figure 3A:
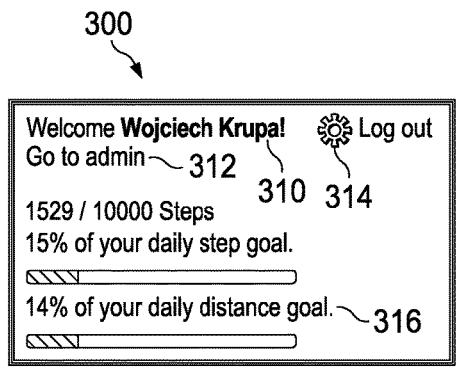
FIG. 3A is an illustration of an employee identification displaying real-time monitoring information within a graphical user interface depicted in accordance with an illustrative embodiment.
Figure 3B:
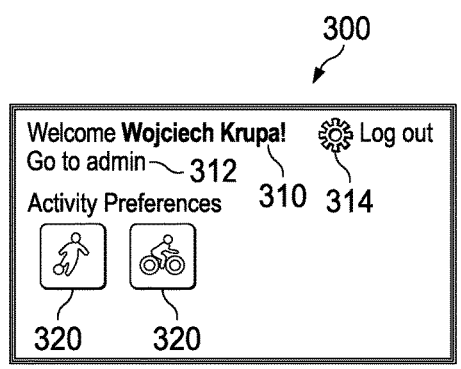
FIG. 3B is an illustration of an employee identification displaying current activity preferences within a graphical user interface depicted in accordance with an illustrative embodiment.

With reference next to FIGS. 3A and 3B, an illustration of an employee identification within a graphical user interface is depicted in accordance with an illustrative embodiment. As depicted, employee identification 300 is an example of employee identification 202 in FIG. 1.

Figure 11:
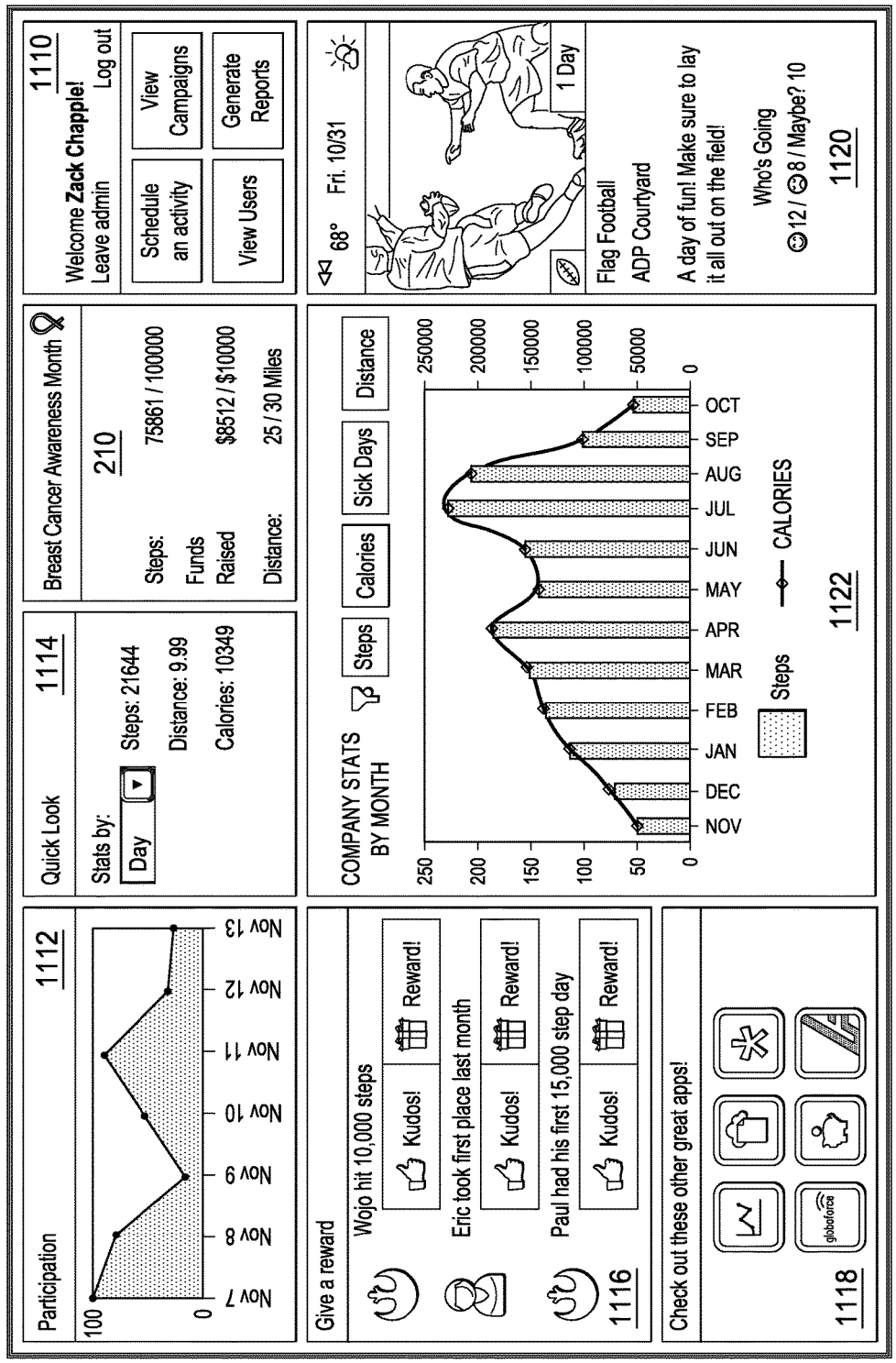
FIG. 11 is an illustration of a graphical user interface for administrator interaction with a wellness management system depicted in accordance with an illustrative embodiment.

Employee identification 300 can include employee 310. Employee 310 is one of employees 104. If employee 310 is also designated as an administrator of wellness management system 102, employee identification 300 can also include link 312 that allows employee 310 to toggle between employee interface 200 and administrator interface 1100 as depicted in FIG. 11 described below. Employee 310 can toggle between real-time monitoring information of FIG. 3A and current activity preferences of FIG. 3B by selecting appropriate icon 314.

Referring now specifically to FIG. 3A, employee identification 300 displays real-time monitoring information for target wellness goals 316 of employee 310. Wellness management system 102 provides wellness goals 316 as a real-time feedback to employee 310 to enable desired level of wellness 112. The real-time monitoring information can be tracked as monitoring information 154 utilizing employee 310's personal fitness tracker 156.

Referring now specifically to FIG. 3B, employee identification 300 displays current activity preferences 320 of employee 310. As depicted, activity preferences 320 are examples of activity preferences 118. Activity preferences 320 indicate specific activities. As depicted, activity preferences 320 indicate a preference for soccer and biking.

Figure 4A:
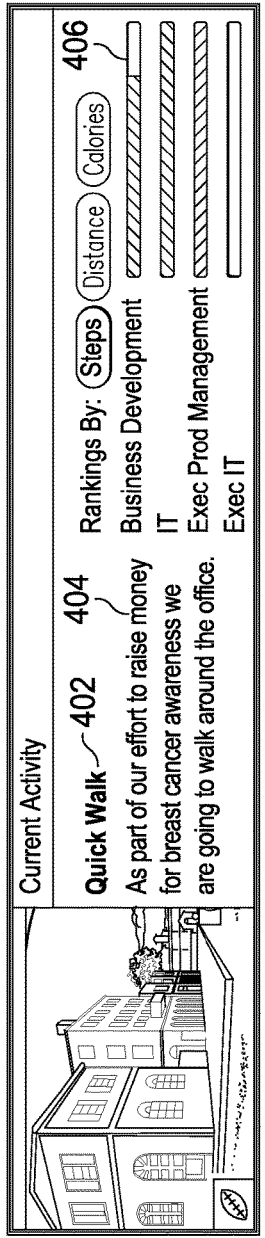
FIG. 4A is an illustration of a current activity ranked according to a number of steps taken by various employee groups within a graphical user interface depicted in accordance with an illustrative embodiment.
Figure 4B:
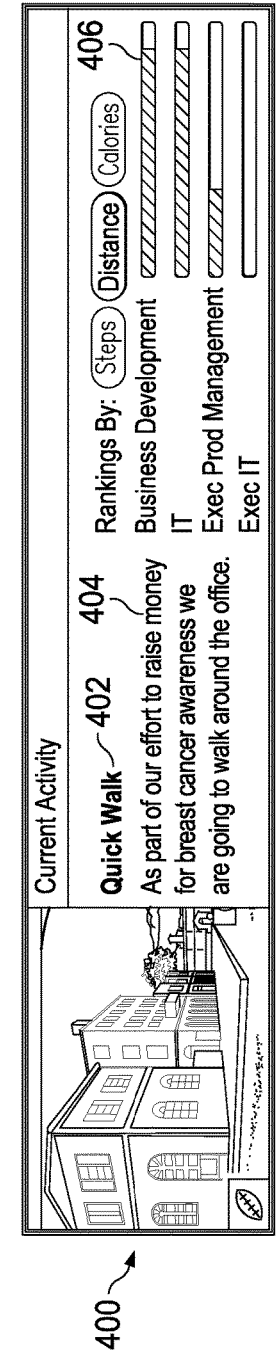
FIG. 4B is an illustration of a current activity ranked according to a distance traveled by various employee groups within a graphical user interface depicted in accordance with an illustrative embodiment.
Figure 4C:
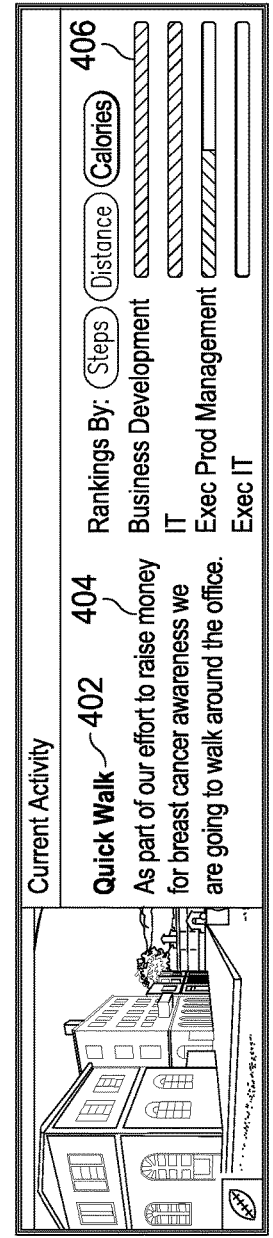
FIG. 4C is an illustration of a current activity ranked according to a number of calories burned by various employee groups within a graphical user interface depicted in accordance with an illustrative embodiment.

With reference next to FIGS. 4A, 4B, and 4C, an illustration of a current activity within a graphical user interface is depicted in accordance with an illustrative embodiment. As depicted, current activity 400 is an example of current activities 204 in FIG. 2. As depicted, current activity 400 can be a display of recommended activity 136, scheduled for a present time based on recommendation 132.

Current activity 400 can include activity title 402. Activity title 402 is a name identifying current recommended activity 136. Current activity 400 can also include activity description 404. Activity description 404 is a short explanation of current activity 400, and can include details such as an indication of recommended location 140, or whether current activity 400 is associated with employer-sponsored campaigns 210.

Current activity 400 can also include activity rankings 406. Activity rankings 406 is a real-time metric displaying a participation ranking of employee groups, such as portion of employees 130, in current activity 400. Activity rankings 406 can rank employee groups by various different parameters. Employee 310 can toggle between the parameters by selecting one of appropriate icons 408.

Referring specifically to FIG. 4A, current activity 400 displays activity rankings 406 ranked according to a number of steps taken by various employee groups, such as portion of employees 130. The number of steps taken can be tracked as monitoring information 154 utilizing pedometer system of personal fitness tracker 156.

Referring specifically to FIG. 4B, current activity 400 displays activity rankings 406 ranked according to a distance traveled by various employee groups, such as portion of employees 130. The distance can be tracked as monitoring information 154 utilizing location monitoring system, such as a global positioning system, of personal fitness tracker 156.

Referring specifically to FIG. 4C, current activity 400 displays activity rankings 406 ranked according to a number of calories burned by various employee groups, such as portion of employees 130. Burned calories can be monitored and displayed, for example as gross calories burned or pro rata calories burned. Burned calories can be tracked as monitoring information 154 of personal fitness tracker 156.

Figure 5A:
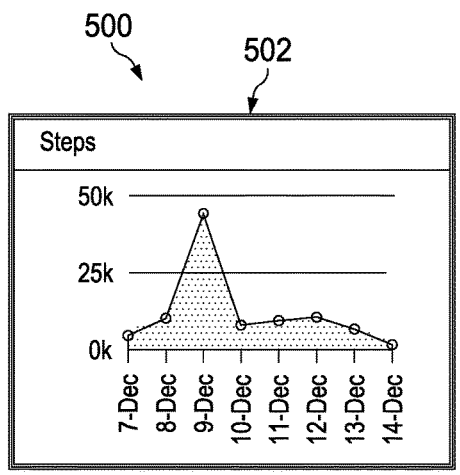
FIG. 5A is an illustration of an employee historic monitoring information showing a breakdown of monitoring information on a daily basis within a graphical user interface depicted in accordance with an illustrative embodiment.
Figure 5B:
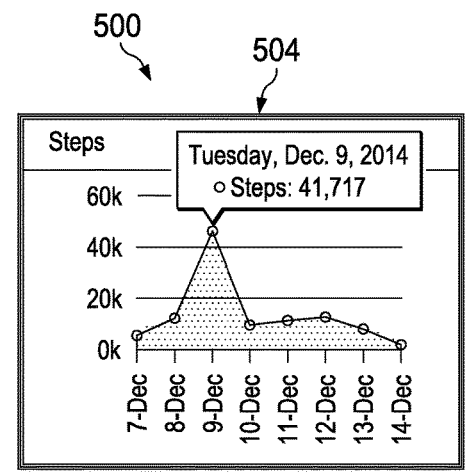
FIG. 5B is an illustration of an employee historic monitoring information showing called out details for a time interval within a graphical user interface depicted in accordance with an illustrative embodiment.

With reference next to FIGS. 5A and 5B, an illustration of employee historic monitoring information within a graphical user interface is depicted in accordance with an illustrative embodiment. As depicted, employee historic monitoring information 500 is an example of employee historic monitoring information 206 in FIG. 2.

Employee historic monitoring information 500 provides a breakdown of monitoring information 154 recorded for employee 310 at previous times. As depicted, employee historic monitoring information 500 displays monitoring information 154 for a number of steps taken during time intervals 502. However, other ones of monitoring information 154, such as a number of calories burned during time intervals 502 or a distance traveled during time intervals 502, could be similarly displayed.

As shown in FIG. 5A, historic monitoring information 500 displays time intervals 502 showing a breakdown of monitoring information 154 on a daily basis. However, other durations for time intervals 502 could also be utilized for displaying historic monitoring information 500.

As shown in FIG. 5B, details 504 for each of the time intervals 502 can be called out by employee 310. For example, details 504 can be called out by clicking, mousing over, or otherwise selecting one of the time intervals 502.

Figure 6:
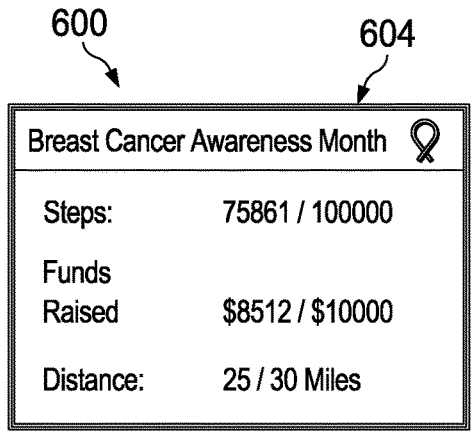
FIG. 6 is an illustration of an employer-sponsored campaigns within a graphical user interface depicted in accordance with an illustrative embodiment.

With reference next to FIG. 6, an illustration of an employer-sponsored campaign within a graphical user interface is depicted in accordance with an illustrative embodiment. As depicted, employer-sponsored campaign 600 is an example of employer-sponsored campaigns 210 in FIG. 2.

Employer-sponsored campaign 600 can include campaign title 602. Campaign title 602 is a name identifying employer-sponsored campaign 600.

Employer-sponsored campaign 600 can also include campaign goals 604. Campaign goals can be, for example one of goals for employees 104 in the aggregate, goals for portion of employees 130, or individual goals for employee 310. Campaign goals 604 can include physical activity goals.

As shown in FIG. 6, campaign goals 604 includes a physical activity goal "steps," and can include a real-time progress toward completion of the goal. Similarly, a physical activity goal "distance" is shown, and can include a real-time progress toward completion of the goal. Progress toward completion of a physical activity goal can be tracked and updated by receiving monitoring information 154 from personal fitness tracker 156.

Campaign goals 604 can include monetary goals. Monetary goals can include, for example at least one of contributions by employees 104, contributions by group of employees 130, contributions by employee 310, or contributions by employer 106. Contributions by employer 106 can be, for example at least one of direct contributions from employer 106, employer contributions based on participation of employees 104 in recommended activities 136, or employer contributions based on completions of other ones of campaign goals 604. As shown in FIG. 6, a monetary goal "funds raised" is shown, and can include a real-time progress toward completion of the goal.

Figure 7A:
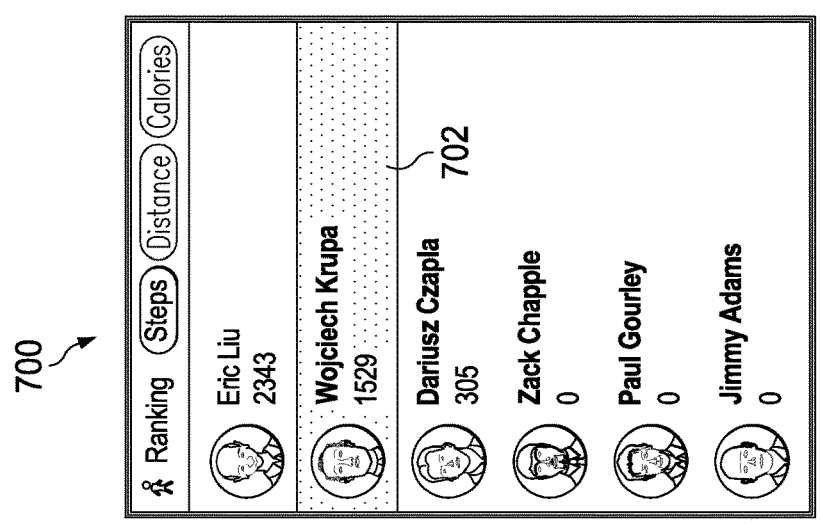
FIG. 7A is an illustration of real-time wellness information showing employees ranked according to a number of steps taken individually within a graphical user interface depicted in accordance with an illustrative embodiment.
Figure 7B:
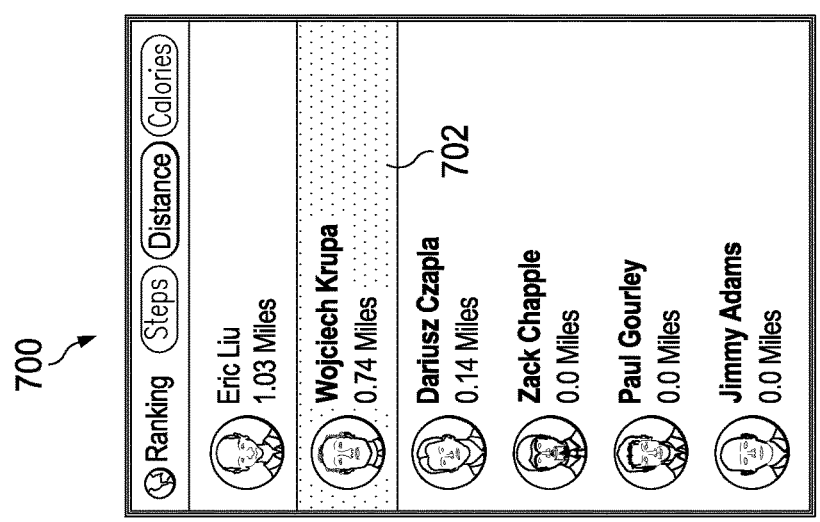
FIG. 7B is an illustration of real-time wellness information showing employees ranked according to a distance traveled individually within a graphical user interface depicted in accordance with an illustrative embodiment.
Figure 7C:
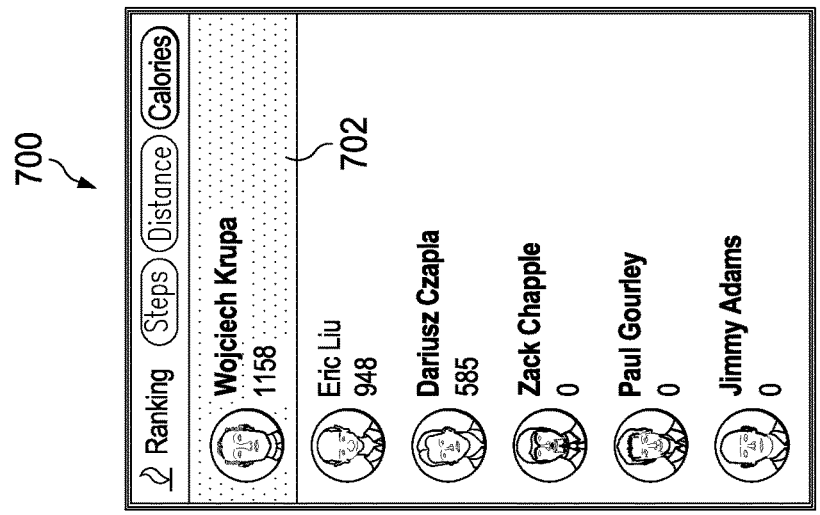
FIG. 7C is an illustration of real-time wellness information showing employees ranked according to a number of calories burned individually within a graphical user interface depicted in accordance with an illustrative embodiment.

With reference next to FIGS. 7A, 7B, and 7C, an illustration of wellness rankings within a graphical user interface is depicted in accordance with an illustrative embodiment. As depicted, wellness rankings 700 is an example of wellness rankings 208 in FIG. 2.

Wellness rankings 700 displays a real-time ranking of employees 104 or group of employees 130 based monitoring information 156 received from personal fitness trackers 156. Wellness rankings 700 displays employee ranking 702 based on cumulative monitoring information 154 received from personal fitness trackers 156 over a predetermined time interval. According to an illustrative embodiment, time interval can be, for example one of daily, weekly, monthly, or other time intervals set by employer 106. According to an illustrative embodiment, the time interval can correspond to a duration of current activity 400. According to an illustrative embodiment, the time interval can correspond to a duration of employer-sponsored campaign 600.

Wellness rankings 700 can rank employees 104 or group of employees 130 by various different parameters. Employee 310 can toggle between the parameters by selecting appropriate one of icons 704.

Referring specifically to FIG. 7A, wellness rankings 700 show employees 104 ranked according to a number of steps taken individually by employees 104. The number of steps taken can be tracked as monitoring information 154 utilizing a pedometer system of personal fitness tracker 156. As shown in FIG. 7A, wellness rankings 700 ranks employee 310 second among employees 104 according to a number of steps taken.

Referring specifically to FIG. 7B, wellness rankings 700 show employees 104 ranked according to a distance traveled individually by employees 104. The distance can be tracked as monitoring information 154 utilizing a location monitoring system, such as a global positioning system, of personal fitness tracker 156. As shown in FIG. 7B, wellness rankings 700 ranks employee 310 second among employees 104 according to a distance traveled.

Referring specifically to FIG. 7C, wellness rankings 700 show employees 104 ranked according to a number of calories burned individually by employees 104. Burned calories can be tracked as monitoring information 154 of personal fitness tracker 156. As shown in FIG. 7C, wellness rankings 700 ranks employee 310 first among employees 104 according to a number of calories burned.

Figure 8:
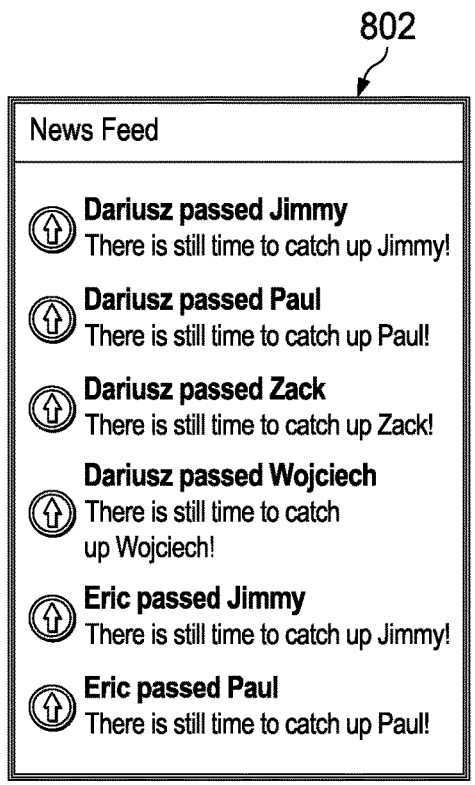
FIG. 8 is an illustration of wellness rankings within a graphical user interface depicted in accordance with an illustrative embodiment.

With reference next to FIG. 8, an illustration of real-time wellness information within a graphical user interface is depicted in accordance with an illustrative embodiment. As depicted, real-time wellness information 800 is an example of real-time wellness information 212 in FIG. 2.

Real-time wellness information 800 provides employee 310 with alerts 802 regarding relative changes in wellness rankings 700 among employees 104. Alerts 802 can be provided in real-time when wellness management system 102 receives monitoring information 154 from personal fitness tracker 156 of ones of employees 104.

Figure 9:
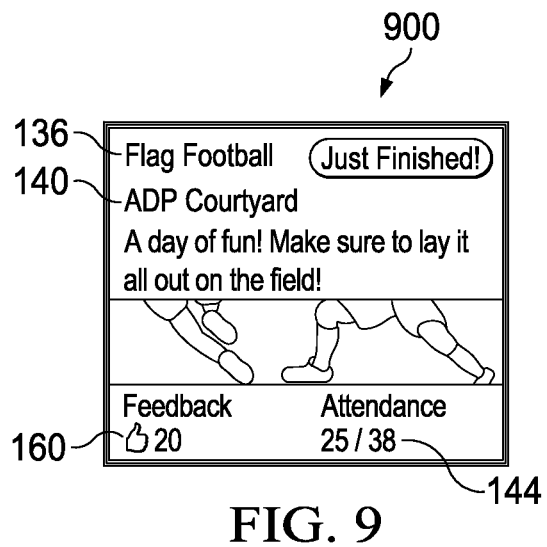
FIG. 9 is an illustration of a previous recommendation within a graphical user interface depicted in accordance with an illustrative embodiment.

With reference next to FIG. 9, an illustration of a previous recommendation within a graphical user interface is depicted in accordance with an illustrative embodiment. As depicted, previous recommendation 900 is an example of previous recommendation 214 in FIG. 2. Previous recommendation 900 is an example of recommendation 132 for recommended activity 136 that has previously occurred at recommended time 138. As depicted, previous recommendation 900 is for a most recent, previously occurring recommended activity 136.

Previous recommendation 900 includes recommended activity 136. As depicted, recommended activity 136 is one of activities 110 that was previously recommended to employee 310. Previous recommendation 900 also includes recommended location 140.

As depicted, previous recommendation 900 also displays feedback opinions 160. As depicted, previous recommendation 900 displays feedback opinions 160 about whether recommended activity 136 was enjoyable to ones of employees 104 that participated in recommended activity 136. However, previous recommendation 900 can also displays feedback opinions 160 regarding, such as for example but not limited to, at least one of a likelihood to participate in identical recommended activities, or a likelihood to participate in similar recommended activities. Feedback opinions 160 can include opinions about recommended location 140, such as for example but not limited to, at least one of opinions about the weather at recommended location 140 during recommended activity 136, opinions about a safety of recommended location 140 during recommended activity 136, opinions about a security of recommended location 140 during recommended activity 136, a likelihood to participate in identical recommended activities at recommended location 140, or a likelihood to participate in similar recommended activities at recommended location 140.

As depicted, previous recommendation 900 also includes participation statistics 144. As depicted, participation statistics 144 is a number employees 104 who registered for and participated in recommended activity 136 of previous recommendation 900. However, previous recommendation 900 can include others of participation statistics 144, such as but not limited to, at least one of a number of employees 104 participating in an activity, a percentage of employees 104 participating in an activity, a number of portion of employees 130 participating in an activity, a percentage of portion of employees 130 participating in an activity, a percentage of employees 104 who registered for and participated in recommended activity 136, a number portion of employees 130 who registered for and participated in recommended activity 136, or a percentage of portion of employees 130 who registered for and participated in recommended activity 136.

Figure 10:
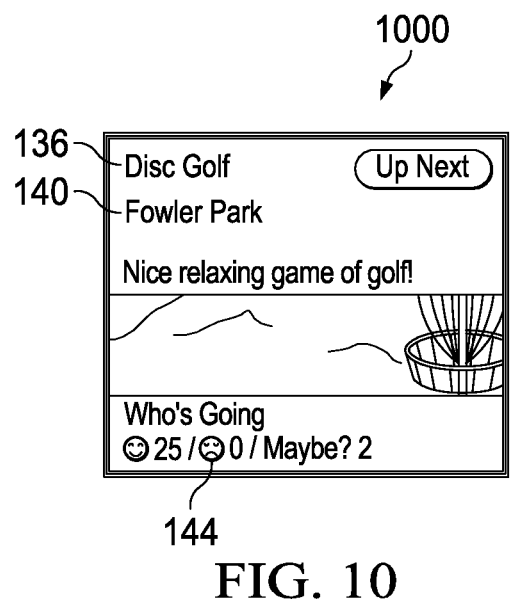
FIG. 10 is an illustration of a upcoming recommendation within a graphical user interface depicted in accordance with an illustrative embodiment.

With reference next to FIG. 10, an illustration of an upcoming recommendation within a graphical user interface is depicted in accordance with an illustrative embodiment. As depicted, upcoming recommendation 1000 is an example of upcoming recommendation 216 in FIG. 2. Upcoming recommendation 1000 is an example of recommendation 132 for recommended activity 136 that will subsequently occur at recommended time 138. As depicted, upcoming recommendation 1000 is for a soonest subsequently occurring recommended activity 136.

Upcoming recommendation 1000 includes recommended activity 136. As depicted, recommended activity 136 is one of activities 110 that is recommended to employee 310. Upcoming recommendation 1000 also includes recommended location 140.

As depicted, upcoming recommendation 1000 also includes participation statistics 144. As depicted, participation statistics 144 is a number of employees 104 registering for recommended activity 136 of upcoming recommendation 1000. However, participation statistics 144 can include other registration statistics such as but not limited to, at least one of, a percentage of employees 104 registering for recommended activity 136, a number of portion of employees 130 registering for recommended activity 136, or a percentage of portion of employees 130 registering for recommended activity 136. Registration statistics can be monitored based on interactions of employees 104 with employee interface 146, indicating an intention to participate in recommended activity 136.

With reference next to FIG. 11, an illustration of a graphical user interface for administrator interaction with a wellness management system is depicted in accordance with an illustrative embodiment. As depicted, administrator interface 1100 is an example of administrator interface 148 of graphical user interface 134 in FIG. 1.

As depicted, administrator interface 1100 can display at least one of administrator identification 1110, historic participation information 1112, wellness metric overview 1114, employer-sponsored campaigns 210, employee incentive allocation 1116, wellness advertisements 1118, recommendations 1120, and wellness metric comparison 1122.

Figure 12:
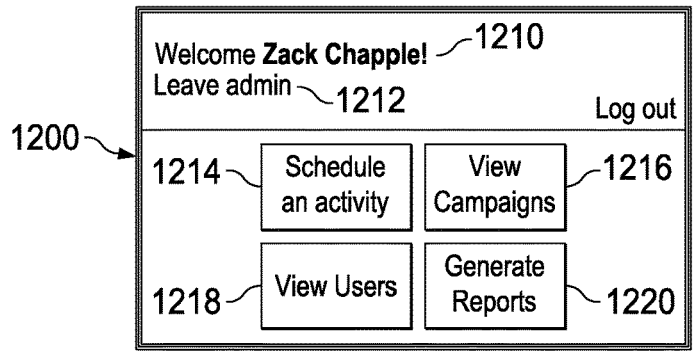
FIG. 12 is an illustration of an administrator identification within a graphical user interface depicted in accordance with an illustrative embodiment.

With reference next to FIG. 12, an illustration of an administrator identification within a graphical user interface is depicted in accordance with an illustrative embodiment. As depicted, administrator interface 1200 is an example of administrator identification 1110 in FIG. 11.

Administrator interface 1200 can include administrator 1210. Administrator 1210 is an administrator of wellness management system 102. Administrator 1210 can also be one of employees 104. When administrator 1210 is one of employees 104, administrator interface 1200 can also include link 1212 to toggle between administrator interface 1100 and employee interface 200.

Administrator 1210 can perform other administrative functions within wellness management system 102 by selecting appropriate icons within administrator interface 1200. As depicted, administrator 1210 can schedule one of activities 110 by selecting icon 1214; administrator 1210 can view employer-sponsored campaigns by selecting icon 1216; administrator 1210 can view employees 104 by selecting icon 1218; and administrator 1210 can generate wellness reports by selecting icon 1220. By selecting one of icons 1214, 1216, 1218, and 1220, administrator 1210 can navigate to an appropriate interface for performing the associated administrative function.

Figure 13:
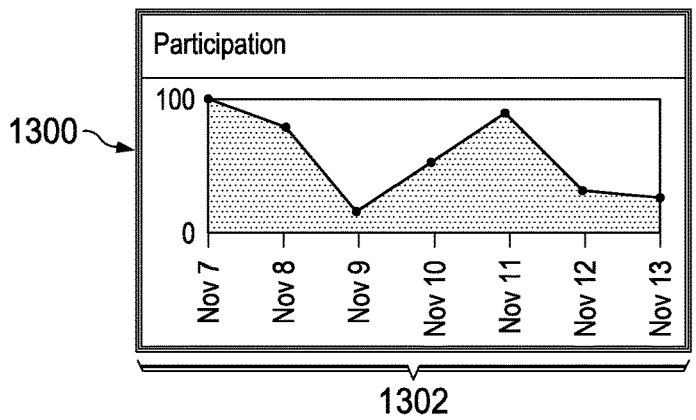
FIG. 13 is an illustration of historic participation information within a graphical user interface depicted in accordance with an illustrative embodiment.

With reference next to FIG. 13, an illustration of historic participation information within a graphical user interface is depicted in accordance with an illustrative embodiment. As depicted, historic participation information 1300 is an example of historic participation information 1112 in FIG. 11. Historic participation information 1300 can be generated from participation statistics 144.

Historic participation information 1300 provides a high-level overview of participation by employees 104 in previously occurring recommended activity 136. As shown, historic participation information 1300 displays time intervals 1302 showing a breakdown of participation by employees 104 in recommended activity 136 on a daily basis. However, other durations for time intervals 1302 could also be utilized for displaying historic participation information 1300. Details for each of the time intervals 1302 can be called out by administrator 1210 by clicking, mousing over, or otherwise selecting one of the time intervals 1302.

Figure 14A:
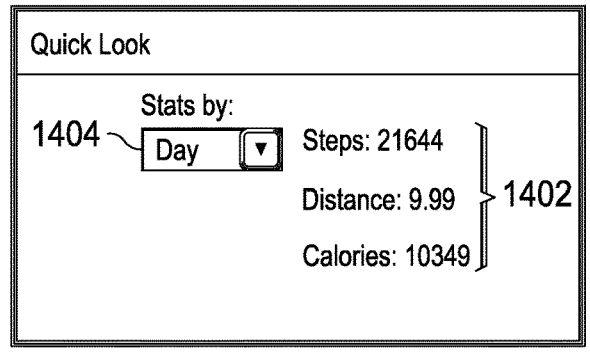
FIG. 14A is an illustration of a wellness metric overview displaying fitness related metrics over a daily time interval within a graphical user interface depicted in accordance with an illustrative embodiment.
Figure 14B:
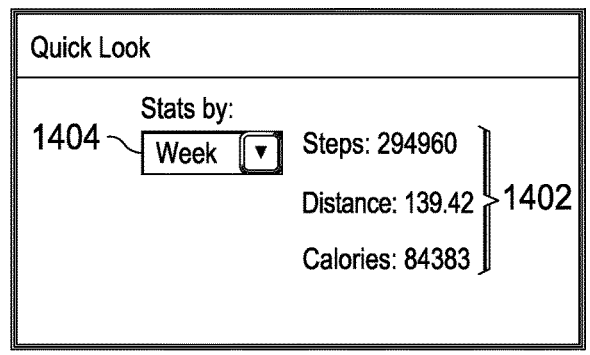
FIG. 14B is an illustration of a wellness metric overview displaying fitness related metrics over a weekly time interval within a graphical user interface depicted in accordance with an illustrative embodiment.
Figure 14C:
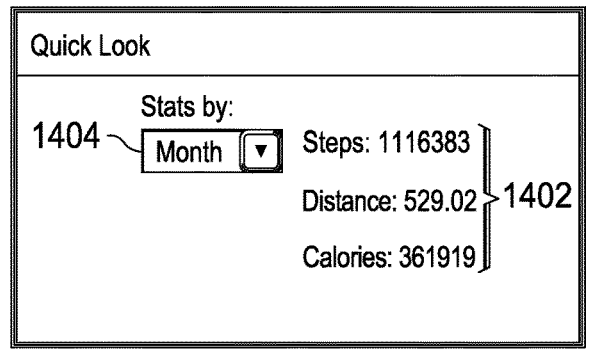
FIG. 14C is an illustration of a wellness metric overview displaying fitness related metrics over a monthly time interval within a graphical user interface depicted in accordance with an illustrative embodiment.

With reference next to FIGS. 14A, 14B, and 14C, an illustration of a wellness metric overview within a graphical user interface is depicted in accordance with an illustrative embodiment. As depicted, wellness metric overview 1400 is an example of wellness metric overview 1114 in FIG. 11.

Wellness metric overview 1400 displays fitness related metrics 1402. Fitness related metrics 1402 can be aggregated and updated in real-time as wellness management system 102 receives monitoring information 154 for employees 104 from personal fitness tracker 156. Fitness related metrics 1402 can show metrics such as but not limited to, at least one of an aggregate number of steps taken by employees 104, an aggregate distance traveled by employees 104, or an aggregate number of calories burned by employees 104.

Wellness metric overview 1400 displays fitness related metrics 1402 based on cumulative monitoring information 154 received over a predetermined time interval. The time interval can be, for example one of daily, weekly, monthly, or other time intervals set by employer 106. Administrator 1210 can view different time intervals by making an appropriate selection, such as from drop-down menu 1404, within wellness metric overview 1400.

Referring specifically to FIG. 14A, wellness metric overview 1400 displays fitness related metrics 1402 over a daily time interval. Fitness related metrics 1402 are updated to reflect cumulative monitoring information 154 received from personal fitness trackers 156 over the selected daily time interval.

Referring specifically to FIG. 14B, wellness metric overview 1400 displays fitness related metrics 1402 over a weekly time interval. Fitness related metrics 1402 are updated to reflect cumulative monitoring information 154 received from personal fitness trackers 156 over the selected weekly time interval.

Referring specifically to FIG. 14C, wellness metric overview 1400 displays fitness related metrics 1402 over a monthly time interval. Fitness related metrics 1402 are updated to reflect cumulative monitoring information 154 received from personal fitness trackers 156 over the selected monthly time interval.

Figure 15:
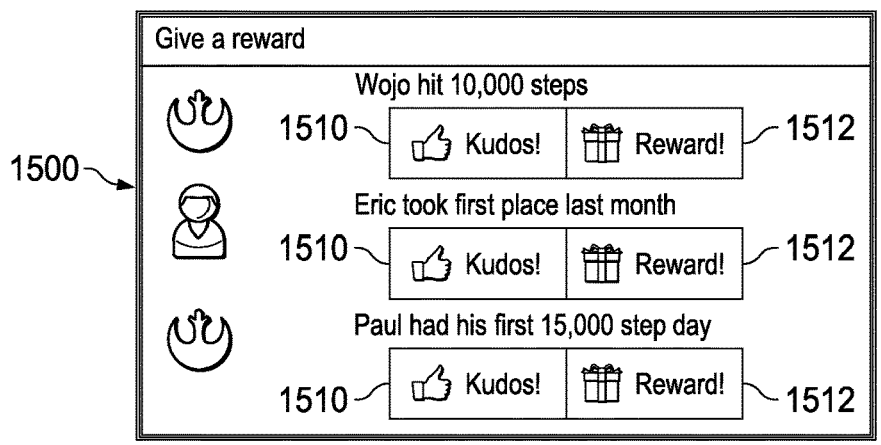
FIG. 15 is an illustration of an employee incentive allocation within a graphical user interface depicted in accordance with an illustrative embodiment.

Referring now to FIG. 15, an illustration of an employee incentive allocation within a graphical user interface is depicted in accordance with an illustrative embodiment. As depicted, employee incentive allocation 1500 is an example of employee incentive allocation 1116 in FIG. 11.

Employee incentive allocation 1500 provides an interface through which administrator 1210 can recognize or reward ones of employees 104 that have attained desired level of wellness 112. Employee incentive allocation 1500 can include recognition icons 1510. Administrator 1210 can select recognition icons 1510 to recognize employees 104 that have attained desired level of wellness 112. Employee incentive allocation 1500 can include reward icon 1512. Administrator 1210 can select reward icon 1512 to reward employees 104 that have attained desired level of wellness 112.

Figure 16A:
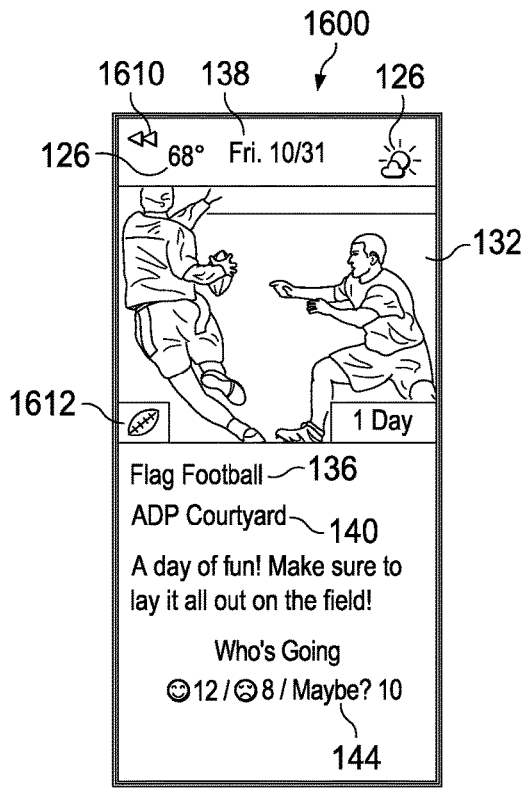
FIG. 16A is an illustration of recommendations shown for a recommended activity that subsequently will occur at a recommended time within a graphical user interface depicted in accordance with an illustrative embodiment.
Figure 16B:
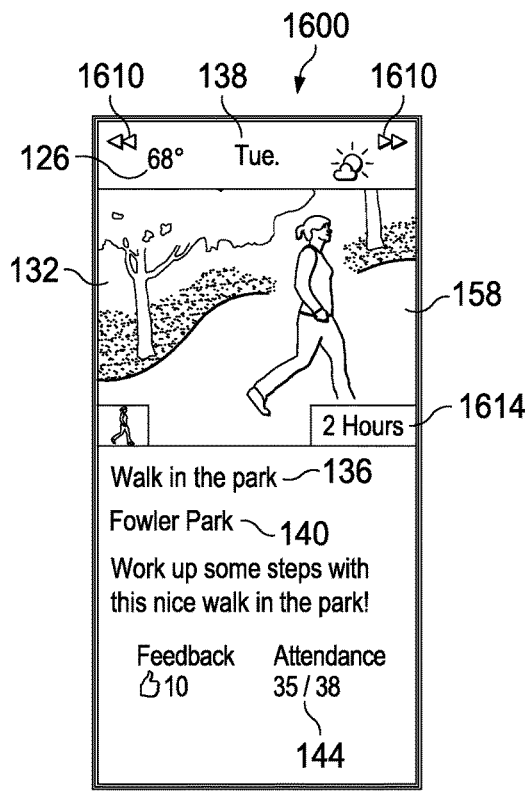
FIG. 16B is an illustration of recommendations shown for a recommended activity that previously occurred at a recommended time within a graphical user interface depicted in accordance with an illustrative embodiment.

With reference next to FIGS. 16A and 16B, an illustration of recommendations within a graphical user interface is depicted in accordance with an illustrative embodiment. As depicted, recommendations 1600 is an example of recommendations 1120 in FIG. 11. Recommendations 1120 are examples of recommendation 132.

Recommendations 1600 can include recommendation 132 for recommended activity 136 that subsequently will occur at recommended time 138. Recommendations 1600 can include recommendation 132 for a recommended activity 136 that has previously occurred at recommended time 138. Administrator 1210 can navigate through recommendations 1600 by selecting navigation icons 1610.

Referring now specifically to FIG. 16A, recommendation 1612 is shown for recommended activity 136 that subsequently will occur at recommended time 138. Recommendation 1612 includes participation statistics 144. As depicted, participation statistics 144 is a number of employees 104 registering for recommended activity 136 of upcoming recommendation 1612. However, participation statistics 144 can include other registration statistics such as but not limited to, at least one of, a percentage of employees 104 registering for recommended activity 136, a number of portion of employees 130 registering for recommended activity 136, or a percentage of portion of employees 130 registering for recommended activity 136. Registration statistics can be monitored based on interactions of employees 104 with employee interface 146, indicating an intention to participate in recommended activity 136.

Recommendation 1612 includes location information 126 for recommended location 140. As depicted, location information 126 includes expected weather conditions for recommended location 140 at recommended time 138.

Referring now specifically to FIG. 16B, recommendation 1614 is shown for recommended activity 136 that previously occurred at recommended time 138. Recommendation 1614 includes participation statistics 144. As depicted, participation statistics 144 is a number employees 104 who registered for and participated in recommended activity 136 of recommendation 1614. However, recommendation 1614 can include others of participation statistics 144, such as but not limited to, at least one of a number of employees 104 participating in recommended activity 136, a percentage of employees 104 participating in recommended activity 136, a number of portion of employees 130 participating in recommended activity 136, a percentage of portion of employees 130 participating in recommended activity 136, a percentage of employees 104 who registered for and participated in recommended activity 136, a number portion of employees 130 who registered for and participated in recommended activity 136, or a percentage of portion of employees 130 who registered for and participated in recommended activity 136.

Recommendation 1614 also includes location statistics 158 and feedback opinions 160. As depicted, location statistics 158 include monitored weather statistics of a measured temperature for recommended location 140 at recommended time 138, and monitored atmospheric conditions for recommended location 140.

With reference next to FIGS. 17A, 17B, 17C, 17D, 17E, 17F, 17G, and 17H, an illustration of wellness metric comparison within a graphical user interface is depicted in accordance with an illustrative embodiment. As depicted, wellness metric comparison 1700 is an example of wellness metric comparison 1122 in FIG. 11.

Wellness metric comparison 1700 displays comparisons between and among monitored metrics 1710. Monitored metrics 1710 can include at least one of fitness related metrics 1402, or other related to metrics relevant to employer 106. Wellness metric comparison 1700 thereby facilitates identification of relationships and correlations among monitored metrics 1710.

As depicted, monitored metrics 1710 include fitness related metrics of an aggregate number of steps taken by employees 104, an aggregate distance traveled by employees 104, or an aggregate number of calories burned by employees 104. Monitored metrics 1710 also includes other related metrics relevant to employer 106 of an aggregate number of sick days taken by employees 104. As depicted, monitored metrics 1710 can be shown individually, or overlain with other monitored metrics 1710 to easily identify relationships and correlations among monitored metrics 1710.

Figure 17A:
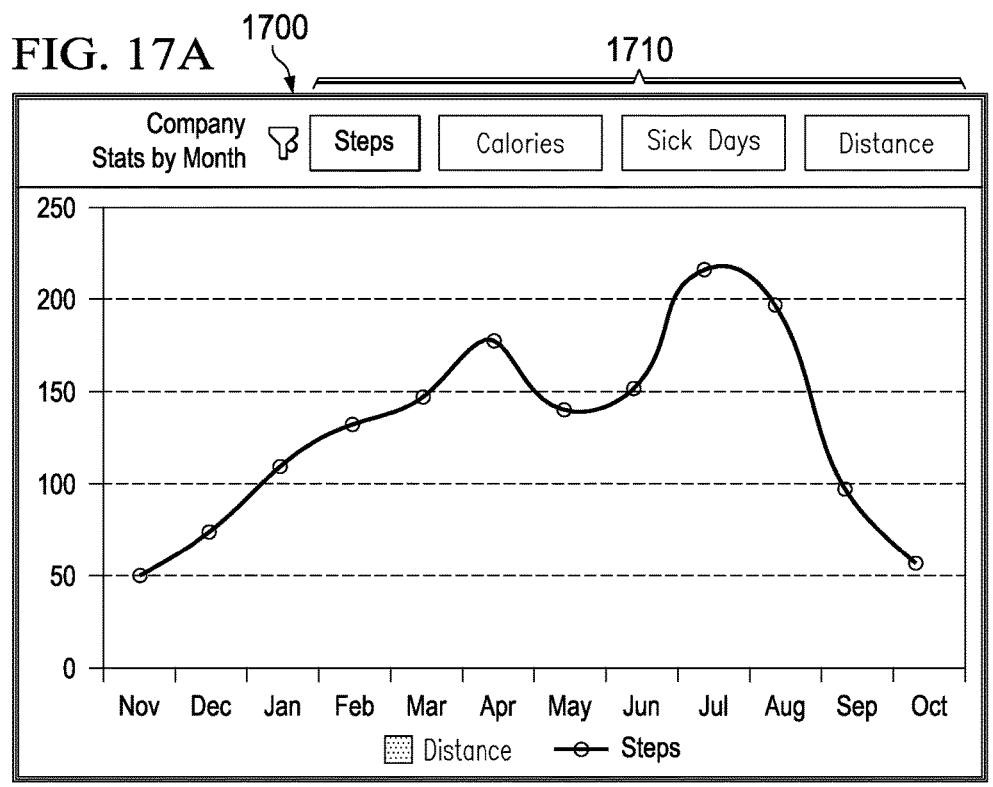
FIG. 17A is an illustration of a wellness metric comparison displaying monitored metrics for an aggregate number of steps taken by employees within a graphical user interface depicted in accordance with an illustrative embodiment.

Referring now specifically to FIG. 17A, wellness metric comparison 1700 individually displays monitored metrics 1710 for an aggregate number of steps taken by employees 104.

Figure 17B:
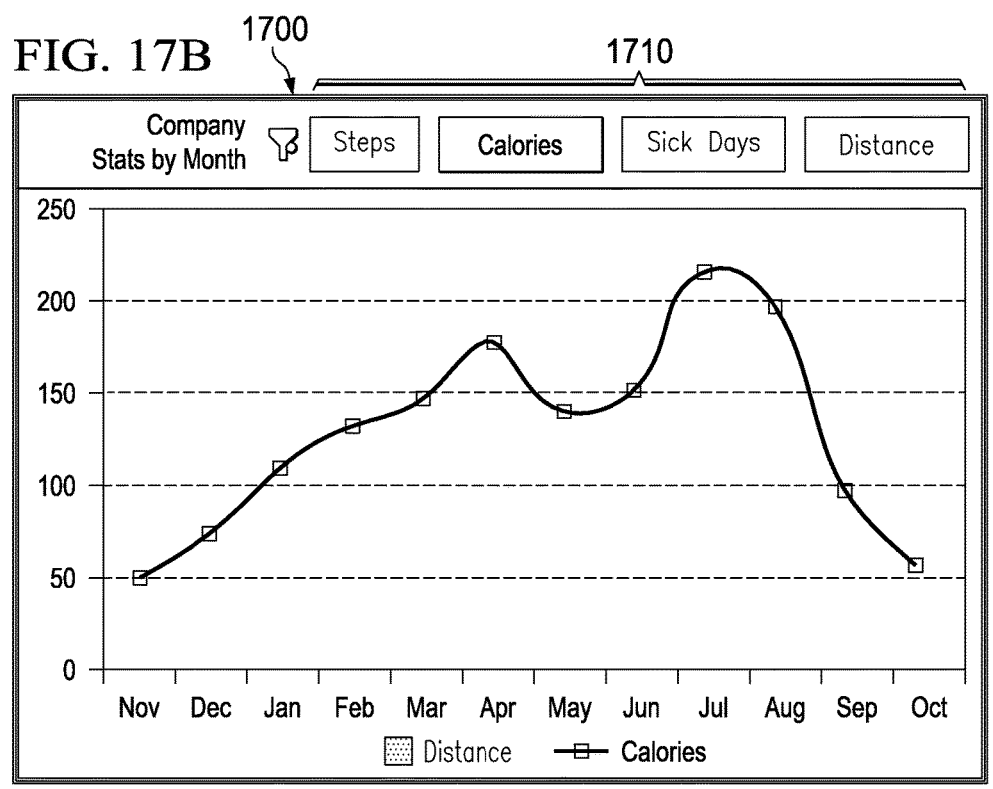
FIG. 17B is an illustration of a wellness metric comparison displaying monitored metrics for an aggregate number of calories burned by employees within a graphical user interface depicted in accordance with an illustrative embodiment.

Referring now specifically to FIG. 17B, wellness metric comparison 1700 individually displays monitored metrics 1710 for an aggregate number of calories burned by employees 104.

Figure 17C:
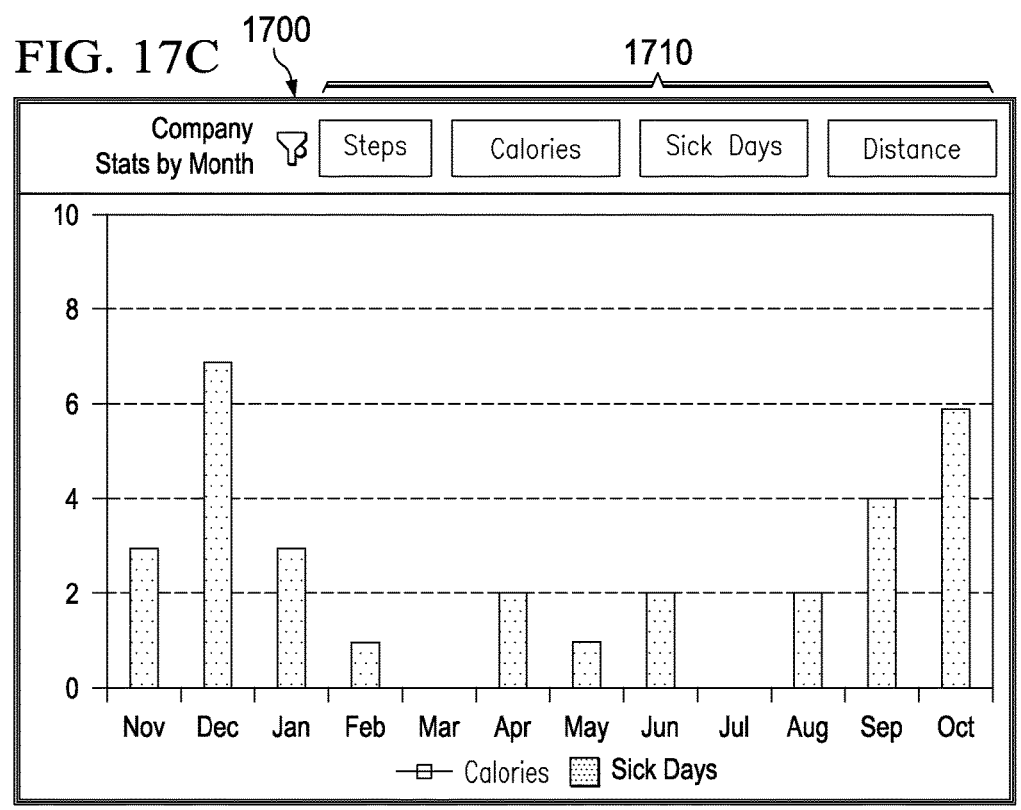
FIG. 17C is an illustration of a wellness metric comparison displaying monitored metrics for an aggregate number of sick days taken by employees within a graphical user interface depicted in accordance with an illustrative embodiment.

Referring now specifically to FIG. 17C, wellness metric comparison 1700 individually displays monitored metrics 1710 for an aggregate number of sick days taken by employees 104.

Figure 17D:
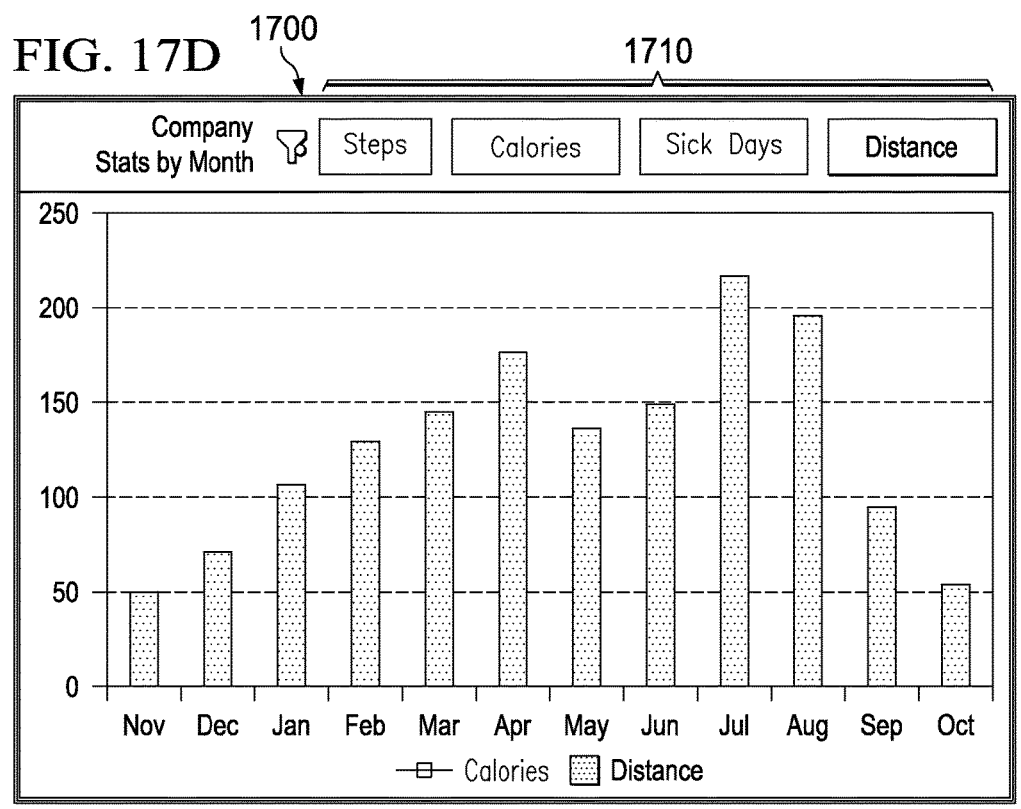
FIG. 17D is an illustration of a wellness metric comparison displaying monitored metrics for an aggregate distance traveled by employees within a graphical user interface depicted in accordance with an illustrative embodiment.

Referring now specifically to FIG. 17D, wellness metric comparison 1700 individually displays monitored metrics 1710 for an aggregate distance traveled by employees 104.

Figure 17E:
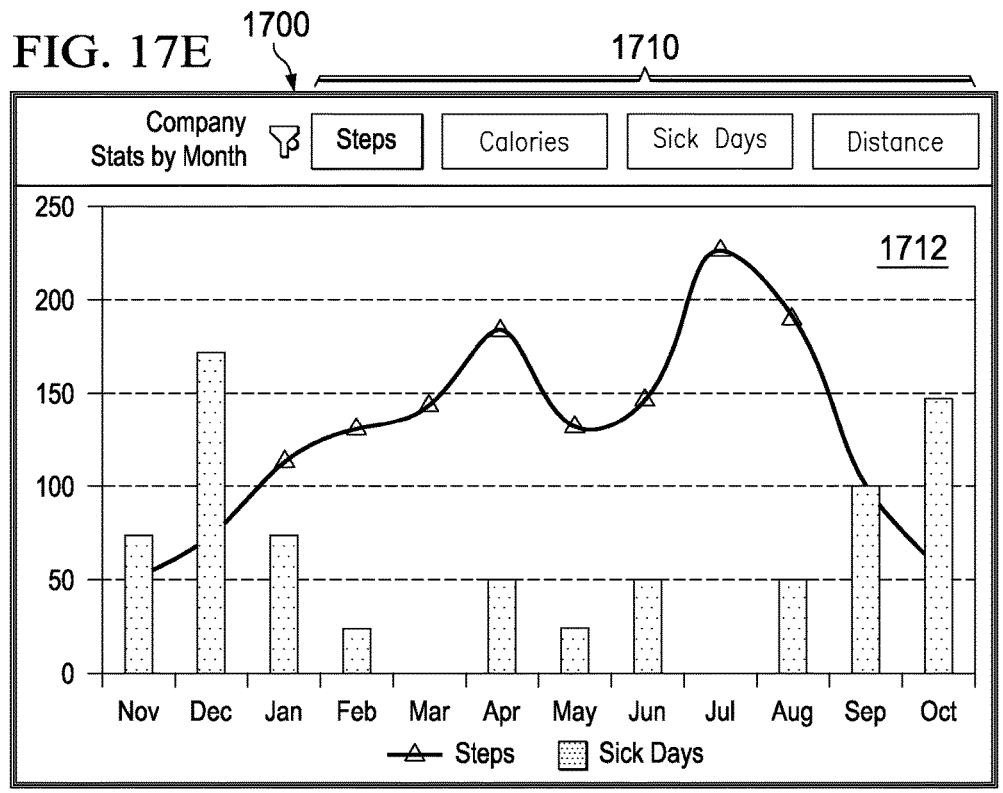
FIG. 17E is an illustration of a wellness metric comparison displaying a comparison of monitored metrics for an aggregate number of steps taken and an aggregate number of sick days taken by employees within a graphical user interface depicted in accordance with an illustrative embodiment.

Referring now specifically to FIG. 17E, wellness metric comparison 1700 displays comparison 1712 of monitored metrics 1710 for an aggregate number of steps taken and an aggregate number of sick days taken by employees 104. Based on comparison 1712, administrator 1210 can identify relationships and correlations between an aggregate number of steps taken and an aggregate number of sick days taken.

Figure 17F:
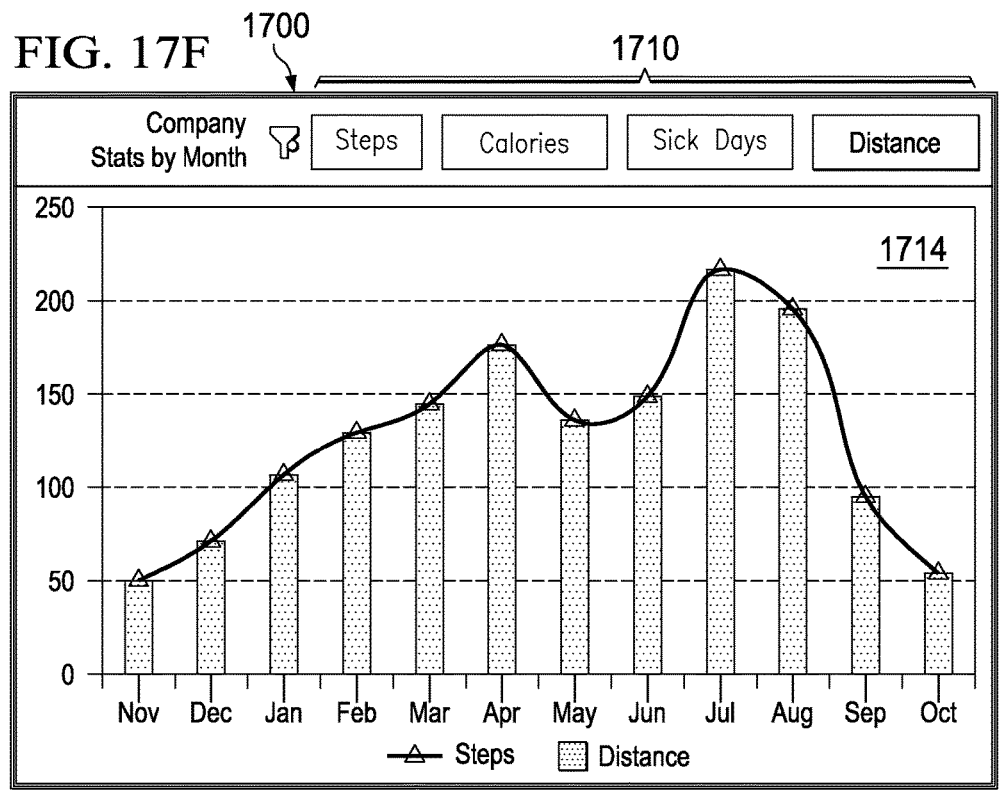
FIG. 17F is an illustration of a wellness metric comparison displaying a comparison of monitored metrics for an aggregate number of steps taken and an aggregate distance traveled by employees within a graphical user interface depicted in accordance with an illustrative embodiment.

Referring now specifically to FIG. 17F, wellness metric comparison 1700 displays comparison 1714 of monitored metrics 1710 for an aggregate number of steps taken and an aggregate distance traveled by employees 104. Based on comparison 1714, administrator 1210 can identify relationships and correlations between an aggregate number of steps taken and an aggregate distance traveled.

Figure 17G:
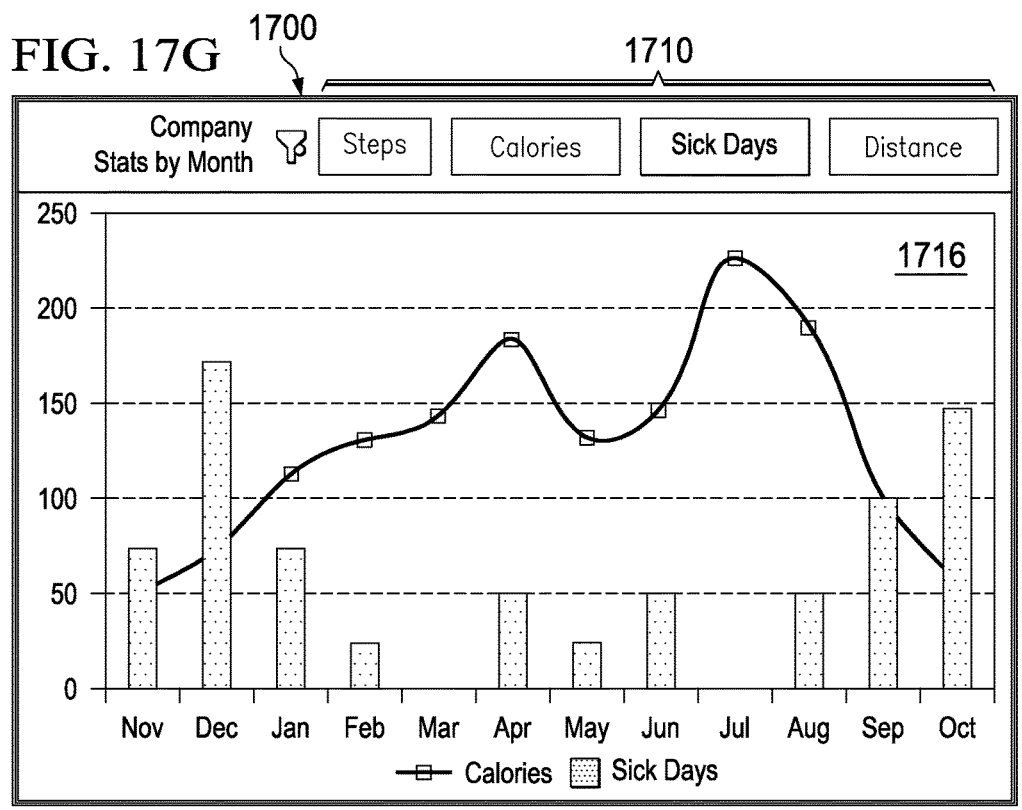
FIG. 17G is an illustration of a wellness metric comparison displaying a comparison of monitored metrics for an aggregate number of calories burned and an aggregate number of sick days taken by employees within a graphical user interface depicted in accordance with an illustrative embodiment.

Referring now specifically to FIG. 17G, wellness metric comparison 1700 displays comparison 1716 of monitored metrics 1710 for an aggregate number of calories burned and an aggregate number of sick days taken by employees 104. Based on comparison 1716, administrator 1210 can identify relationships and correlations between an aggregate number of calories burned and an aggregate number of sick days taken.

Figure 17H:
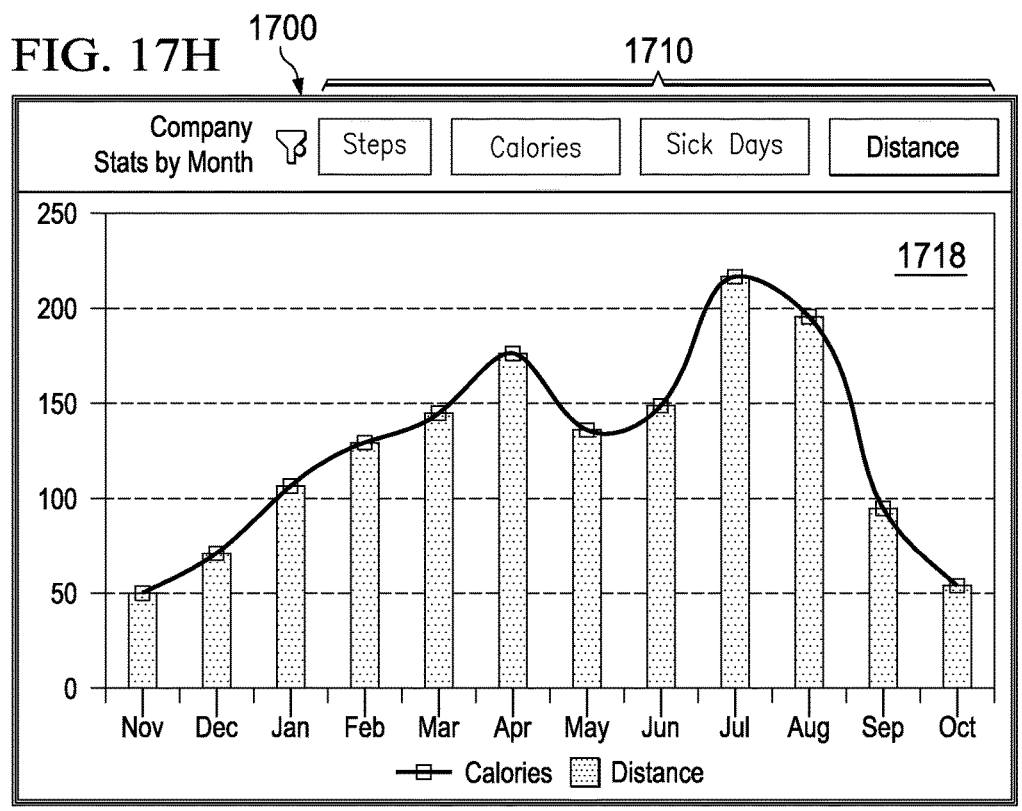
FIG. 17H is an illustration of a wellness metric comparison displaying a comparison of monitored metrics for an aggregate number of calories burned and an aggregate distance traveled by employees within a graphical user interface depicted in accordance with an illustrative embodiment.

Referring now specifically to FIG. 17H, wellness metric comparison 1700 displays comparison 1718 of monitored metrics 1710 for an aggregate number of calories burned and an aggregate distance traveled by employees 104. Based on comparison 1718, administrator 1210 can identify relationships and correlations between an aggregate number of calories burned and an aggregate distance traveled.

Figure 18A:
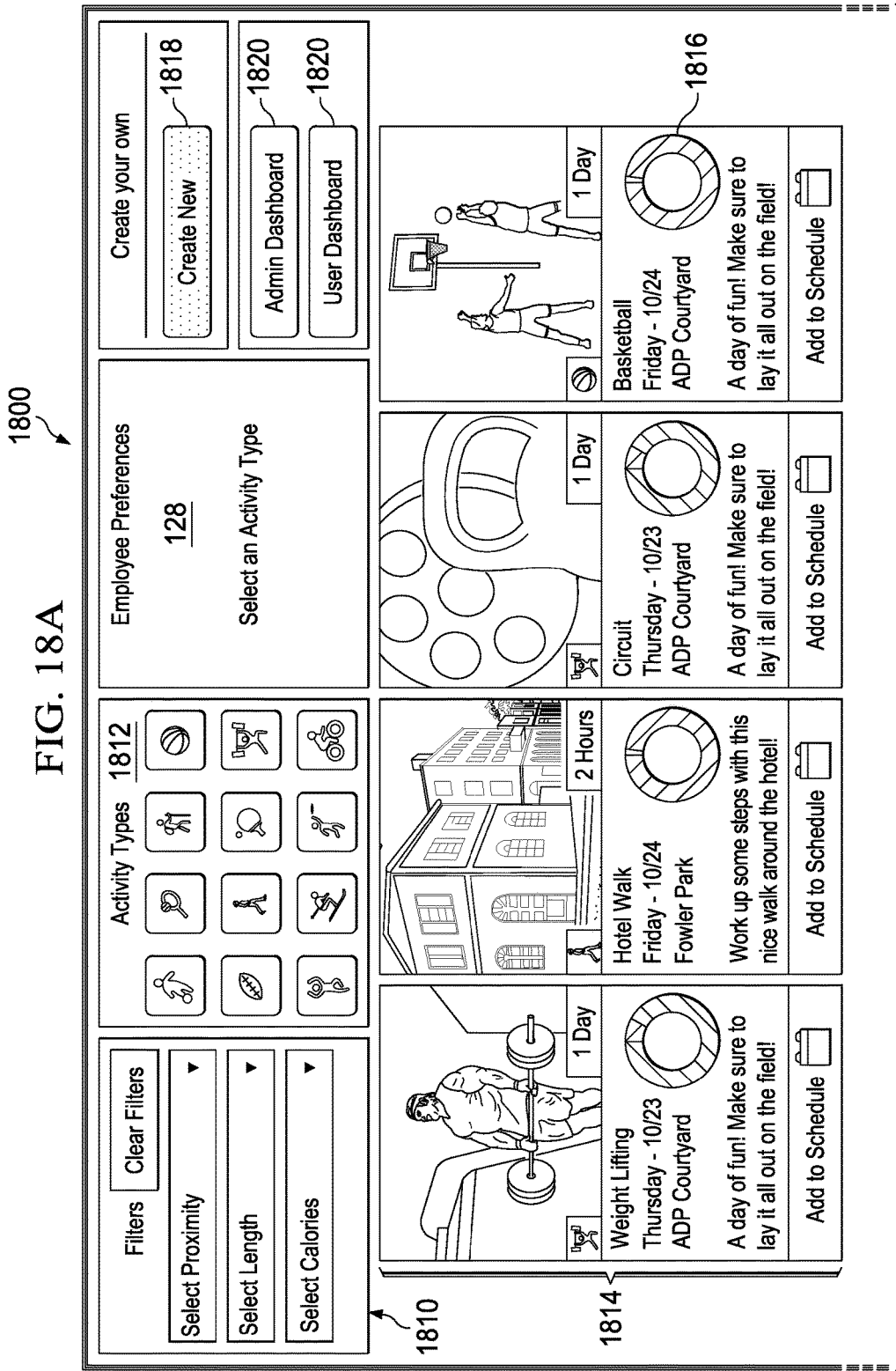
FIG. 18A is a partial view of an illustration of an activity scheduling interface for administrator interaction with a wellness management system depicted in accordance with an illustrative embodiment.
Figure 18B:
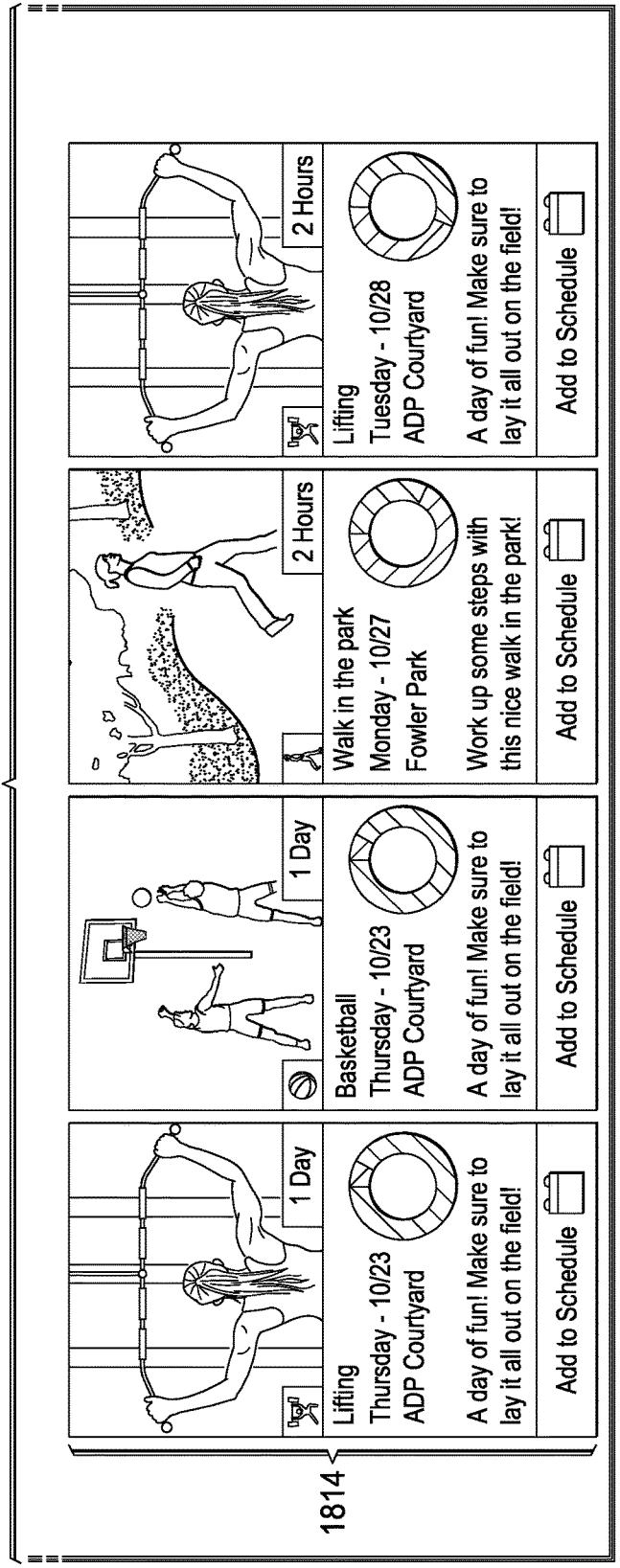
FIG. 18B is a partial view of an illustration of an activity scheduling interface for administrator interaction with a wellness management system depicted in accordance with an illustrative embodiment.

Referring now to FIGS. 18A and 18B, an illustration of an activity scheduling interface for administrator interaction with a wellness management system is depicted in accordance with an illustrative embodiment. As depicted, activity scheduling interface 1800 is an example of administrator interface 146 of graphical user interface 134 in FIG. 1. As depicted, administrator 1210 can use activity scheduling interface 1800 to schedule activities 110 or make recommendations 132. As depicted, administrator 1210 can navigate to activity scheduling interface 1800 by selecting icon 1214 from administrator interface 1200.

As depicted, activity scheduling interface 1800 can display at least one of activity filters 1810, activity types 1812, aggregate activity preferences 128, recommended activities 1814, recommendation 1816, and activity creation icon 1818. Activity scheduling interface 1800 can also include appropriate icons 1820, allowing administrator 1210 to navigate to administrator interface 1200 or employee interface 200.

Referring now to FIGS. 19A, 19B, 19C, and 19D, an illustration of an activity filter within a graphical user interface is depicted in accordance with an illustrative embodiment. As depicted, activity filter 1900 is an example of activity filter 1810 of activity scheduling interface 1800 in FIG. 18.

Figure 19A:
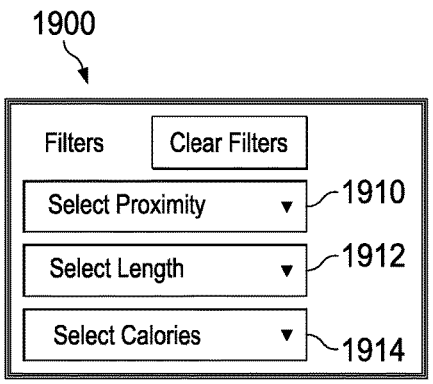
FIG. 19A is an illustration of activity filters within a graphical user interface depicted in accordance with an illustrative embodiment.

Referring now specifically to FIG. 19A, activity filter 1900 provides at least one selectable option through which administrator 1210 can filter activities 110 according to at least one of, health self-assessment data 114, health diagnostic data 116, activity preferences 118, location information 126, or aggregate activity preferences 128. As depicted, activity filter 1900 includes activity proximity filter 1910, activity duration filter 1912, and activity caloric filter 1914. As depicted, activity proximity filter 1910, activity duration filter 1912, and activity caloric filter 1914 are shown as drop-down menus from which administrator 1210 can filter activities 110. However, other methods of inputting filter selections can also be implemented.

Figure 19B:
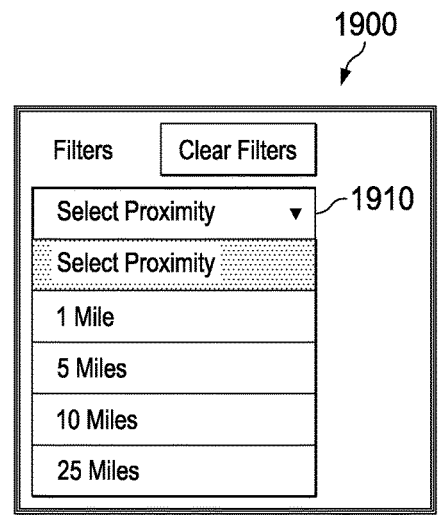
FIG. 19B is an illustration of activity filters showing a drop-down menu selectable option for filtering activities according to a geographical proximity of corresponding locations within a graphical user interface depicted in accordance with an illustrative embodiment.

Referring now specifically to FIG. 19B, activity proximity filter 1910 shows in a drop-down menu selectable option through which administrator 1210 can filter activities 110 according to a geographical proximity of corresponding locations 125. As depicted, proximity filter 1910 can filter activities 110 based on a distance of corresponding locations 125 from some a relevant location, such as a physical location of employer 106, a building at which employer 106 has physical operations, other location relevant to portion of employees 130 or employer 106, or any other location having portion of employees 130 within the selected geographical proximity. As depicted, proximity filter 1910 can filter activities based on corresponding locations 125 that are a distance of 1 mile, 5 miles, 10 miles, or 25 miles from a relevant location.

The geographical proximity shown in proximity filter 1910 corresponds to location information 126 for locations 120. Proximity filter 1910 allows wellness management system 102 to utilize location information 126 to make recommendations 132. Wellness management system 102 can further utilize proximity filter 1910 with a scheduled location of employees 104 to identify portion of employees 130 to receive recommendation 132.

Figure 19C:
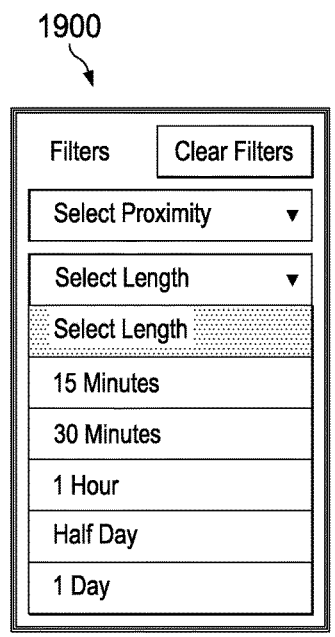
FIG. 19C is an illustration of activity filters showing a drop-down menu selectable option for filtering activities according to an activity duration within a graphical user interface depicted in accordance with an illustrative embodiment.

Referring now specifically to FIG. 19C, activity duration filter 1912 shows in a drop-down menu selectable option through which administrator 1210 can filter activities 110 according to an activity duration. As depicted, activity duration filter 1912 can filter activities based on a duration of 15 minute activities, 30 minute activities, one hour activities, half-day activities, or full-day activities.

The activity durations of activity duration filter 1912 correspond to health factors 122 for activities 110. Activity duration filter 1912 facilitates wellness management system 102 utilization of health factors 122 to make recommendations 132. Wellness management system 102 can further utilize activity duration filter 1912 with activity preferences 118 of employees 104 to identify portion of employees 130 to receive recommendation 132.

Figure 19D:
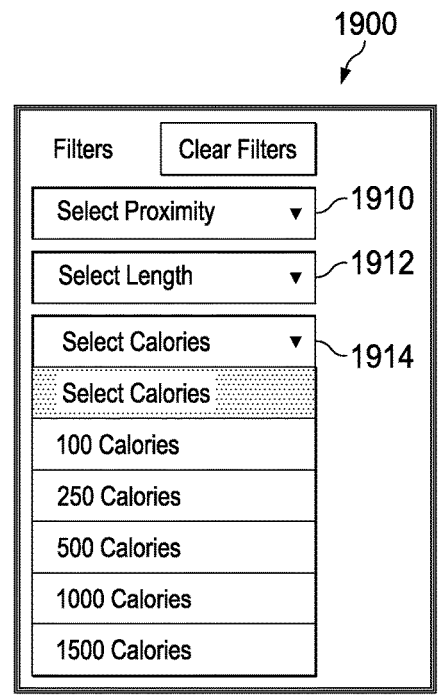
FIG. 19D is an illustration of activity filters showing a drop-down menu selectable option for filtering activities according to an expected caloric expenditure within a graphical user interface depicted in accordance with an illustrative embodiment.

Referring now specifically to FIG. 19D, activity caloric filter 1914 shows in a drop-down menu selectable option through which administrator 1210 can filter activities 110 according to an expected caloric expenditure. As depicted, activity caloric filter 1914 can filter activities based on an expected calorie expenditure of 100 calories, 250 calories, 500 calories, 1000 calories, or 1500 calories.

The expected caloric expenditures of activity caloric filter 1914 correspond to health factors 122 for activities 110. Activity caloric filter 1914 facilitates wellness management system 102 utilization of health factors 122 to make recommendations 132. Wellness management system 102 can further utilize activity caloric filter 1914 with activity preferences 118 of employees 104 to identify portion of employees 130 to receive recommendation 132.

Referring now to FIGS. 20A, 20B, 20C, 20D, 20E, 20F, 20G, 20H, and 20I, an illustration of activity types and aggregate activity preferences within a graphical user interface is depicted in accordance with an illustrative embodiment. As depicted, activity types 2010 is an example of activity types 1812 of activity scheduling interface 1800 in FIG. 18. As depicted, aggregate activity preferences 2012 is an example of aggregate activity preferences 128 of activity scheduling interface 1800 in FIG. 18.

Activity types 2010 are specific ones of activities 110. As depicted, activity types 2010 include soccer, football, yoga, frisbee, walking, basketball, tennis, table tennis, biking, skiing, weightlifting, or hiking. Activity types 2010 correspond to activity preferences 320 of FIG. 3B, a selection of which indicates a preference by employee 310 for the indicated specific activity.

Aggregate activity preferences 2012 is aggregate activity preferences 128. Aggregate activity preferences 2012 indicate an aggregated preference of employees 104 for activity types 2010.

Figure 20A:
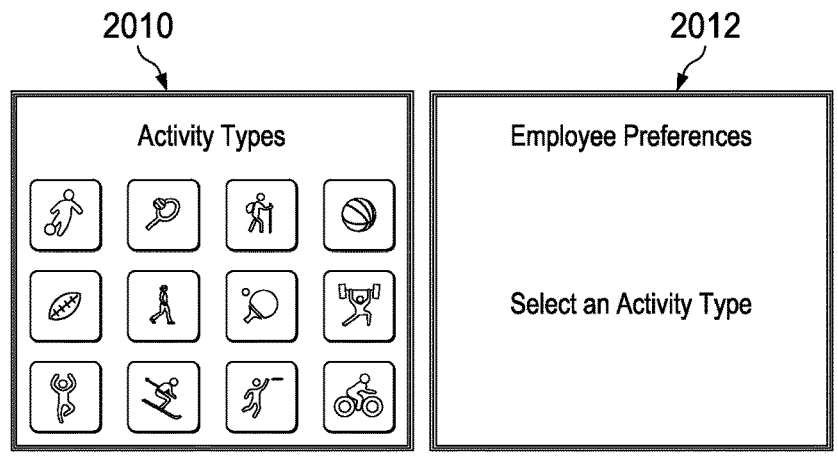
FIG. 20A is an illustration of activity types and aggregate activity preferences within a graphical user interface depicted in accordance with an illustrative embodiment.

Referring now specifically to FIG. 20A, aggregate activity preferences 2012 is displayed without selecting activity types 2010. Because none of aggregate activity preferences 2012 are selected, no preference is indicated within aggregate activity preferences 2012.

Figure 20B:
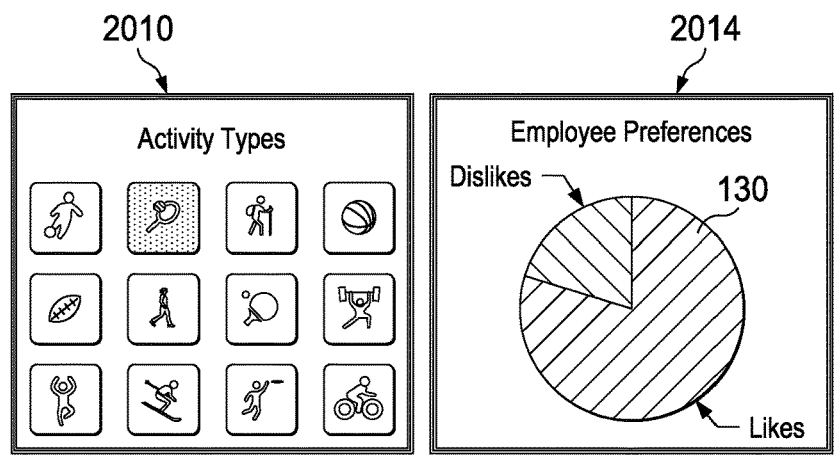
FIG. 20B is an illustration of activity types and aggregate activity preferences showing a selection of a single activity type within a graphical user interface depicted in accordance with an illustrative embodiment.

Referring now specifically to FIG. 20B, aggregate activity preferences 2012 is displayed showing a selection of a single one of activity types 2010. As depicted, the selected one of activity types 2010 is tennis. Based on the selection of activity type 2010, wellness management system 102 updates aggregate activity preferences 2012 to graphically indicate aggregate activity preference 128 of employees 104 for tennis. From aggregate activity preferences 2012 displayed in FIG. 20B, administrator 1210 can easily identify that a majority of employees 104 are included in portion of employees 130 indicating activity preferences 118 for tennis. Because tennis is an activity preferred by a large portion of employees 130, wellness management system 102 can preferentially make recommendation 132 for recommended activity 136 of tennis to portion of employees 130 in order to maximize participation in recommended activity 136.

Figure 20C:
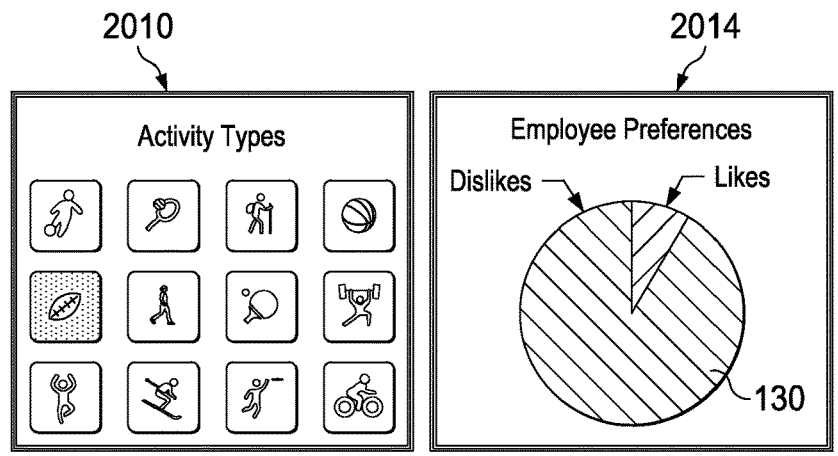
FIG. 20C is an illustration of activity types and aggregate activity preferences showing a selection of a single activity type within a graphical user interface depicted in accordance with an illustrative embodiment.

Referring now specifically to FIG. 20C, aggregate activity preferences 2012 is displayed showing a selection of a single one of activity types 2010. As depicted, the selected one of activity types 2010 is football. Based on the selection of activity type 2010, wellness management system 102 updates aggregate activity preferences 2012 to graphically indicate aggregate activity preference 128 of employees 104 for football. From aggregate activity preferences 2012 in FIG. 20c, administrator 1210 can easily identify that a minority of employees 104 are included in portion of employees 130 indicating activity preferences 118 for football. Because football is not an activity preferred by a large portion of employees 130, wellness management system 102 can preferentially not make recommendation 132 for a recommended activity 136 of football to portion of employees 130 in order to maximize participation in recommended activity 136. However, if portion of employees 130 indicating activity preferences 118 for football is a statistically relevant portion of employees 130, wellness management system 102 may still make recommendation 132 for recommended activity 136 of football to portion of employees 130.

Figure 20D:
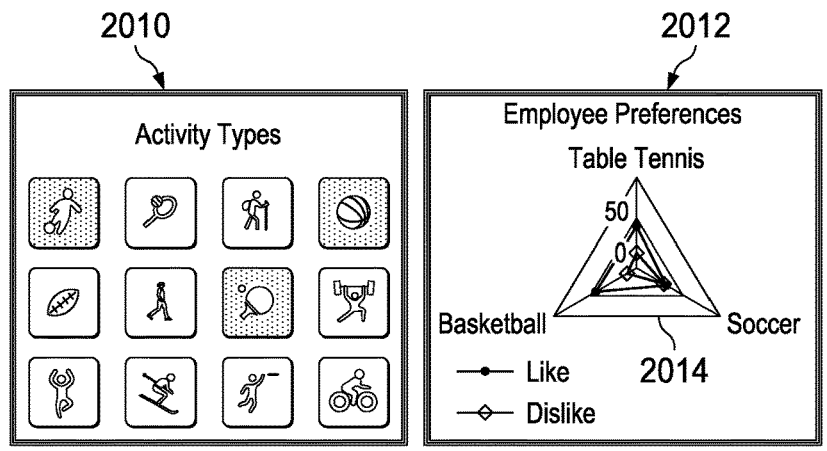
FIG. 20D is an illustration of activity types and aggregate activity preferences showing a selection of multiple activity types within a graphical user interface depicted in accordance with an illustrative embodiment.

Referring now specifically to FIG. 20D, aggregate activity preferences 2012 is displayed showing a selection of a multiple ones of activity types 2010. As depicted, the selected ones of activity types 2010 are soccer, basketball, and table tennis. Based on the selection of multiple ones of activity type 2010, wellness management system 102 updates aggregate activity preferences 2012 to graphically indicate aggregate activity preference 128 of employees 104 for activity types 2010 of soccer, basketball, and table tennis.

As shown in FIG. 20D, aggregate activity preferences 2012 are displayed in the form of polar chart 2014. Polar chart 2014 is an example of polar chart 150 of graphical user interface 134 in FIG. 1. Polar chart 2014 is a comparison of three different ones of activity types 2010. As depicted, polar chart 2014 is a comparison of activity types 2010 of soccer, basketball, and table tennis.

Figure 20E:
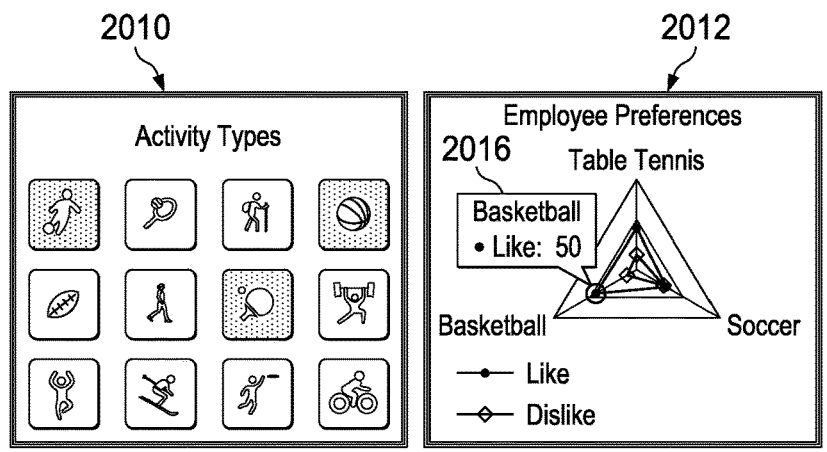
FIG. 20E is an illustration of activity types and aggregate activity preferences showing a selection of multiple activity types and called out details for data points within a graphical user interface depicted in accordance with an illustrative embodiment.

Referring now specifically to FIG. 20E, aggregate activity preferences 2012 is displayed showing a selection of a multiple ones of activity types 2010. As depicted, details 2016 for each of the data points on polar chart 2014 can be called out by administrator 1210. For example, details 2016 can be called out by clicking, mousing over, or otherwise selecting one of activity types 2010 from within activity preferences 2012.

From polar chart 2014 in FIGS. 20D and 20E, administrator 1210 can easily identify portion of employees 130 that has indicated a preference or dislike for each of the selected activity types 2010. Additionally, administrator 1210 can easily identify which of the selected activity types 2010 are preferred by a greater number of employees 104. Wellness management system 102 can therefore include a greater number of employees 104 in portion of employees 130 when making recommendation 132.

By identifying ones of activity types 2010 that are most preferred among employees 104, wellness management system 102 can more often make recommendations 132 for those activity types that are most preferred. Therefore, as depicted, wellness management system 102 may make recommendation 132 for a recommended activity 136 of basketball more often than recommendation 132 for the recommended activity 136 of table tennis.

Figure 20F:
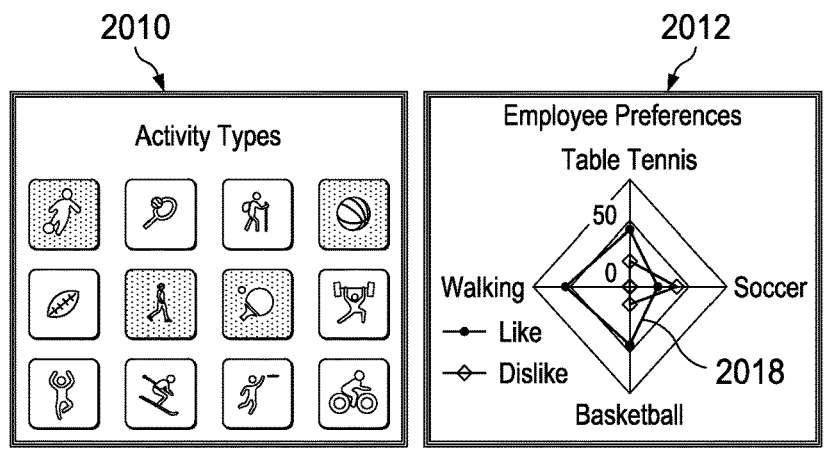
FIG. 20F is an illustration of activity types and aggregate activity preferences showing a selection of multiple activity types within a graphical user interface depicted in accordance with an illustrative embodiment.

Referring now specifically to FIG. 20F, aggregate activity preferences 2012 is displayed showing a selection of a multiple ones of activity types 2010. As depicted, the selected ones of activity types 2010 are soccer, basketball, table tennis, and walking. Based on the selection of activity type 2010, wellness management system 102 updates aggregate activity preferences 2012 to graphically indicate aggregate activity preference 128 of employees 104 for soccer, basketball, table tennis, and walking.

As shown in FIG. 20F, aggregate activity preferences 2012 are displayed in the form of polar chart 2018. Polar chart 2018 is an example of polar chart 150 of graphical user interface 134 in FIG. 1. Polar chart 2018 is a comparison of four different ones of activity types 2010.

Figure 20G:
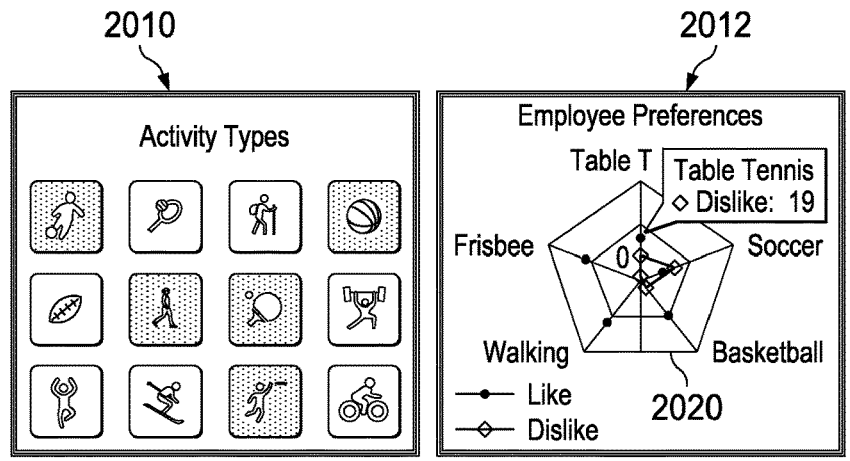
FIG. 20G is an illustration of activity types and aggregate activity preferences showing a selection of multiple activity types within a graphical user interface depicted in accordance with an illustrative embodiment.

Referring now specifically to FIG. 20G, aggregate activity preferences 2012 is displayed showing a selection of a multiple ones of activity types 2010. As depicted, the selected ones of activity types 2010 are soccer, basketball, table tennis, walking, and Frisbee. Based on the selection of activity type 2010, wellness management system 102 updates aggregate activity preferences 2012 to graphically indicate aggregate activity preference 128 of employees 104 for soccer, basketball, table tennis, walking, and Frisbee.

As shown in FIG. 20G, aggregate activity preferences 2012 are displayed in the form of polar chart 2020. Polar chart 2020 is an example of polar chart 150 of graphical user interface 134 in FIG. 1. Polar chart 2020 is a comparison of five different ones of activity types 2010.

Figure 20H:
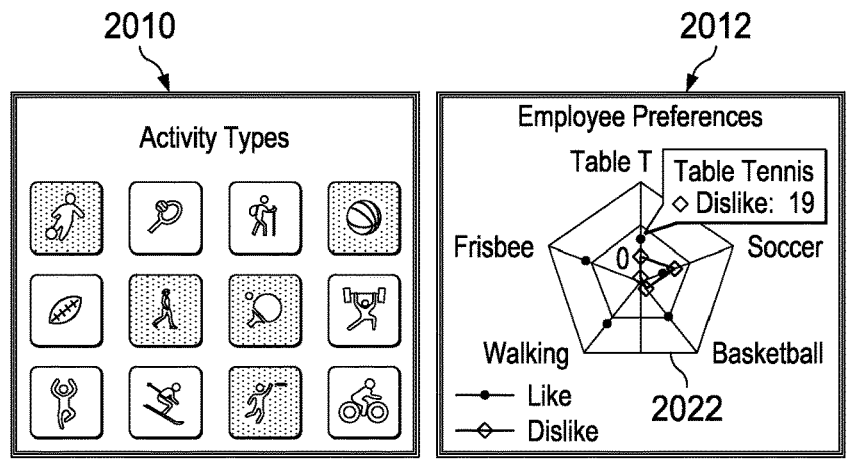
FIG. 20H is an illustration of activity types and aggregate activity preferences showing a selection of multiple activity types within a graphical user interface depicted in accordance with an illustrative embodiment.

Referring now specifically to FIG. 20H, aggregate activity preferences 2012 is displayed showing a selection of a multiple ones of activity types 2010. As depicted, the selected ones of activity types 2010 are soccer, basketball, table tennis, walking, Frisbee, and yoga. Based on the selection of activity type 2010, wellness management system 102 updates aggregate activity preferences 2012 to graphically indicate aggregate activity preference 128 of employees 104 for soccer, basketball, table tennis, walking, frisbee, and yoga.

As shown in FIG. 20H, aggregate activity preferences 2012 are displayed in the form of polar chart 2022. Polar chart 2022 is an example of polar chart 150 of graphical user interface 134. Polar chart 2022 is a comparison of six different ones of activity types 2010.

Figure 20I:
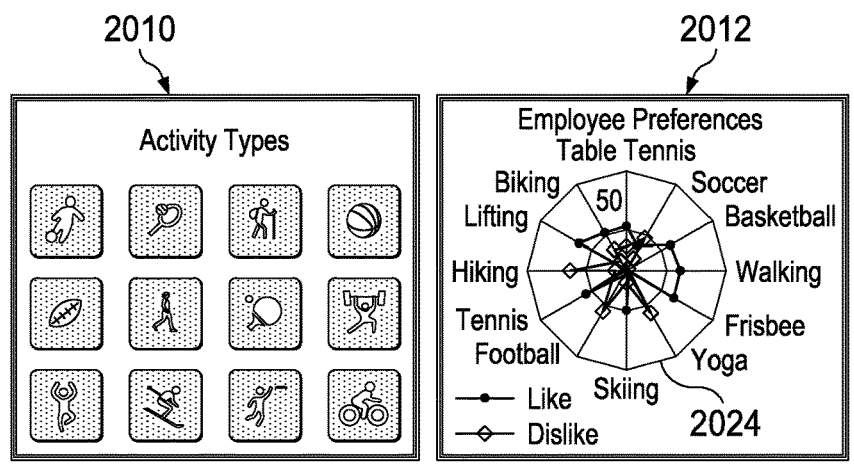
FIG. 20I is an illustration of activity types and aggregate activity preferences showing a selection of all activity types within a graphical user interface depicted in accordance with an illustrative embodiment.

Referring now specifically to FIG. 20I, aggregate activity preferences 2012 is displayed showing a selection of all of activity types 2010. As depicted, the selected ones of activity types 2010 are soccer, football, yoga, frisbee, walking, basketball, tennis, table tennis, biking, skiing, weightlifting, and hiking. Based on the selection of activity type 2010, wellness management system 102 updates aggregate activity preferences 2012 to graphically indicate aggregate activity preference 128 of employees 104 for each of activity types 2010.

As shown in FIG. 20I, aggregate activity preferences 2012 are displayed in the form of polar chart 2024. Polar chart 2024 is an example of polar chart 150 of graphical user interface 134. Polar chart 2024 is a comparison of all (twelve) of activity types 2010.

Polar charts 2014, 2018, 2020, 2022, and 2024 allows administrator 1210 to easily identify portion of employees 130 that has indicated a preference or dislike for each of the selected activity types 2010. Additionally, administrator 1210 can easily identify which of the selected activity types 2010 are preferred by a greater number of employees 104. Wellness management system 102 can therefore include a greater number of employees 104 in portion of employees 130 when making recommendation 132.

Polar chart 2014, polar chart 2018, polar chart 2020, polar chart 2022, and polar chart 2024 display aggregate activity preferences 2012. However, polar charts 150 similar to polar chart 2014, polar chart 2018, polar chart 2020, polar chart 2022, and polar chart 2024 can be used to display other information and statistics, such as but not limited to, at least one of health factors 122, location information 126, aggregate activity preferences 128, participation statistics 144, activity statistics 152, and location statistics 158. Polar charts 150 can be implemented within either employee interface 146 or administrator interface 148.

By displaying aggregate activity preferences 2012 in polar charts 2014, 2018, 2020, 2022, and 2024, wellness management system 102, and administrators utilizing administrator interface 148 can quickly determine at least one of normalities, similarities, or outliers among aggregate activity preferences 2012.

Additionally, wellness management system 102 can preferentially make recommendation 132 for recommended activity 136 indicated in polar charts 2014, 2018, 2020, 2022, and 2024 as preferred by a larger portion of employees 130 in order to maximize participation. For example, aggregate activity preferences 2012 as shown in polar chart 2018, 2020, 2022, and 2024 indicates that a large portion of employees 130 has indicated an activity preference 118 for activity 110 of "walking." Wellness management system 102 can preferentially make recommendation 132 for recommended activity 136 of "walking."

Similarly, wellness management system 102 can preferentially not make recommendation 132 for recommended activity 136 indicated in polar charts 2014, 2018, 2020, 2022, and 2024 as not preferred by a larger portion of employees 130. For example, wellness management system 102 can preferentially not make recommendation 132 for recommended activity 136 of hiking, as shown in polar chart 2024.

By locating similar or dissimilar ones of aggregate activity preferences 2012 within polar charts in polar charts 2014, 2018, 2020, 2022, and 2024, wellness management system 102 can make recommendation 132 to employees 104 for recommended activity 136 that are similar to, but not necessarily indicated by, activity preferences 118 for that employee.

By locating outliers among aggregate activity preferences 2012 within polar charts in polar charts 2014, 2018, 2020, 2022, and 2024, wellness management system 102 can identify at least one of health factors 122 that is common among the uncharacteristic popular or unpopular activity preferences 2012. Wellness management system 102 can then make recommendation 132, giving preference for activities 110 that share health factors 122 common among the uncharacteristic popular or unpopular activity preferences 2012. Wellness management system 102 can make recommendation 132, negatively weighting activities 110 that do not share health factors 122 common among the uncharacteristic popular or unpopular activity preferences 2012.

Figure 21A:
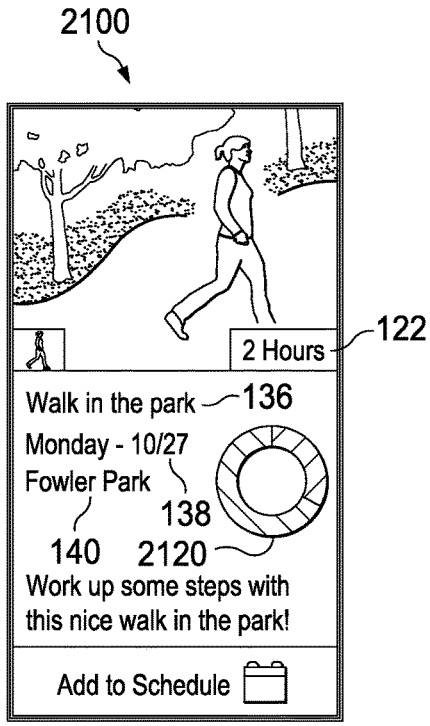
FIG. 21A is an illustration of a recommendation including availability statistics within a graphical user interface depicted in accordance with an illustrative embodiment.
Figure 21B:
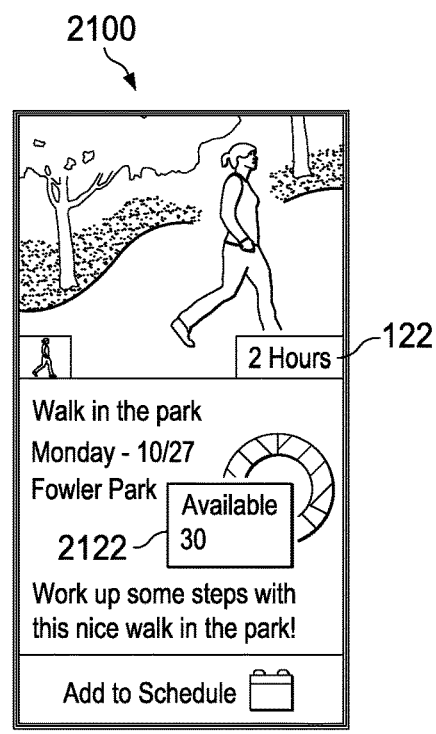
FIG. 21B is an illustration of a recommendation including availability statistics and called out details indicating a number of employees that are available to participate during a recommended time within a graphical user interface depicted in accordance with an illustrative embodiment.
Figure 21C:
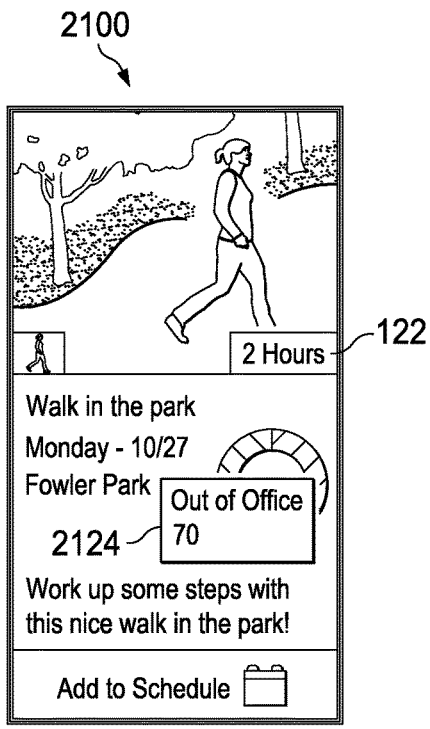
FIG. 21C is an illustration of a recommendation including availability statistics and called out details indicating a number of employees that are not available to participate during a recommended time within a graphical user interface depicted in accordance with an illustrative embodiment.

With reference next to FIGS. 21A, 21B, and 21C, an illustration of a recommendation within a graphical user interface is depicted in accordance with an illustrative embodiment. As depicted, recommendation 2100 is an example of recommended activities 1814 within activity scheduling interface 1800 in FIG. 18. Recommendation 2100 is an example of recommendation 132 in FIG. 1.

As administrator 1210 makes selections from activity filter 1900, wellness management system 102 filters recommended activities 1814 from activity scheduling interface 1800 having health factors 122 that do not match current selections from activity filter 1900. Only activities 110 having health factors 122 that match current activity filter 1900 selections are displayed in recommended activities 1814. Activities 110 having health factors 122 that do not match current activity filter 1900 selections are not displayed in recommended activities 1814.

Recommendation 2100 provides with administrator 1210 with a specific one of various ones of activities 110 that can be scheduled or recommended according to current activity filter 1900 selections. Recommendation 2100 includes recommended activity 136. As depicted, recommended activity 136 is one of activities 110 that matches current activity filter 1900 selections. Recommendation 2100 also includes recommended time 138, and recommended location 140. Recommendation 2100 can also include health factors 122 for recommended activity 136, such as a duration of recommended activity 136.

Referring now specifically to FIG. 21A, recommendation 2100 as depicted, also includes availability statistics 2120. Wellness management system 102 can identify availability statistics 2120 based on availability information parsed from calendar applications for employees 104. In this manner, wellness management system 102 can account for scheduled vacation days, personal days, sick days, times during which business activities or meetings are scheduled for employees 104, times during which employees 104 are geographically remote from recommended location 140, times during which others of activities 110 are scheduled for employees 104, or other conflicting engagements that might impede employees 104 or portion of employees 130 from participating in recommended activity 136 of recommendation 2100.

Referring now specifically to FIG. 21B, details 2122 for availability statistics 2120 can be called out by administrator 1210. For example, details 2122 can be called out by clicking, mousing over, or otherwise selecting one of availability statistics 2120. As depicted, details 2122 indicates a number of employees 104 that are available to participate in, or are otherwise not engaged during recommended time 138 of recommendation 2100.

Referring now specifically to FIG. 21C, details 2124 for availability statistics 2120 can be called out by administrator 1210. As depicted, details 2122 indicates a number of employees 104 that are not available to participate in, or are otherwise engaged during a recommended time 138 of recommendation 2100.

Figures 22, 23:
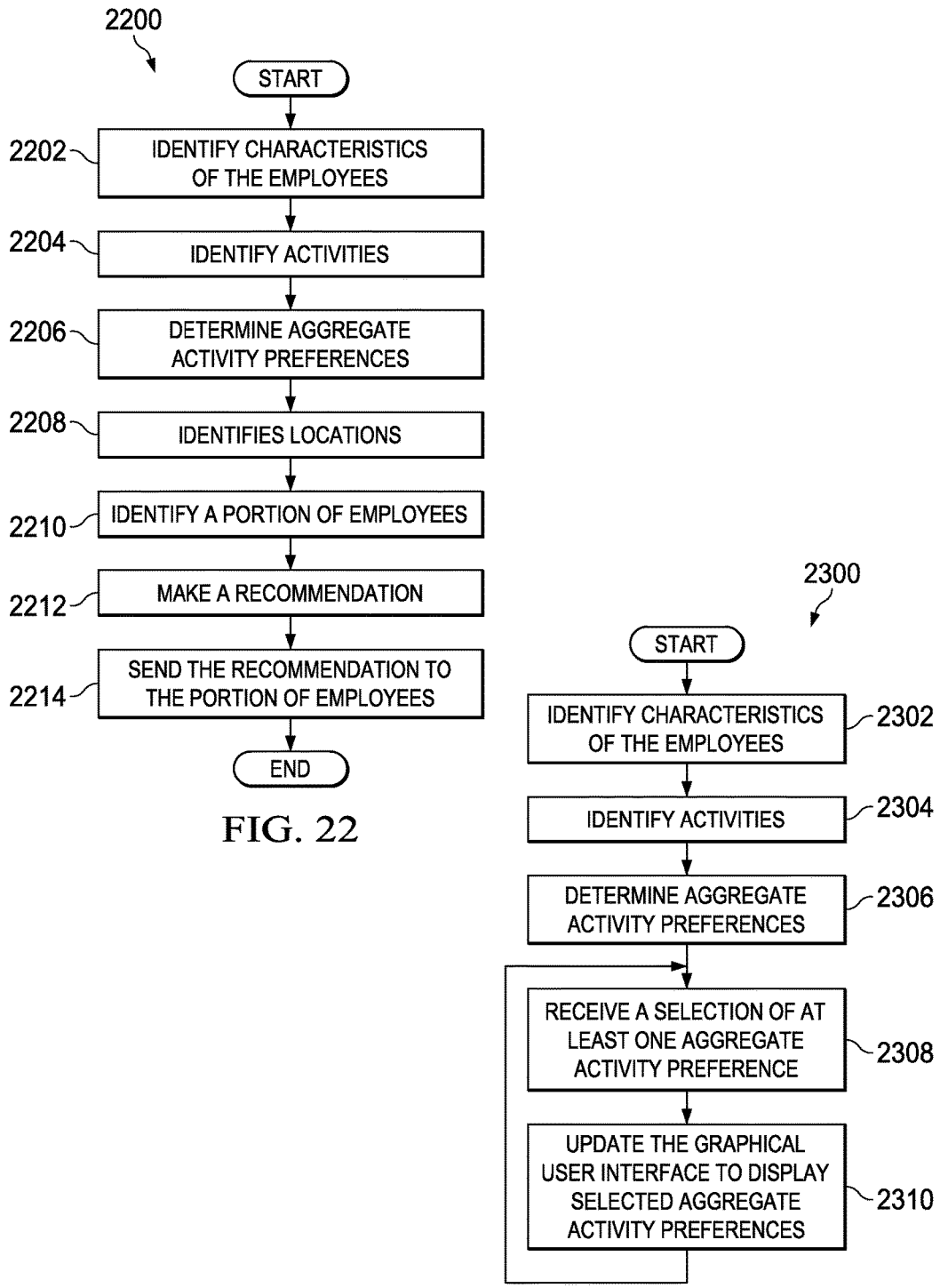
FIG. 22 is an illustration of a flowchart of a process for recommending activities to achieve a desired level of wealth of wellness among employees depicted according to an illustrative embodiment.
FIG. 23 is an illustration of a flowchart of a process for displaying activity preferences within a graphical user interface to achieve a desired level of wealth of wellness among employees is depicted according to an illustrative embodiment.

With reference next to FIG. 22, an illustration of a flowchart of a process for recommending activities to achieve a desired level of wealth of wellness among employees is shown according to an illustrative embodiment. Process 2200 may be implemented in wellness manager 129 in wellness management system 102 in wellness management environment 100 in FIG. 1.

Process 2200 begins by identifying characteristics of the employees (operation 2202). The characteristics are tracked information about the employees that can be used to schedule activities. The characteristics can be characteristics 108 in FIG. 1.

Process 2200 identifies activities (operation 2204). The identified activities are a listing of physical activities, actions, or exercises that wellness management system 102 can recommend to employees 104 in order to achieve a desired level of wellness 112. The identified activities can be activities 110 in FIG. 1. The activities can be identified based on health factors of the activities, such as health factors 122 in FIG. 1.

Based on identified characteristics and identified activities, process 2200 determines aggregate activity preferences (operation 2206). The aggregate activity preferences can be statistical calculations, statistical weights, or other values that indicate an aggregated opinion of employees for various activities. The aggregate activity preferences can be aggregate activity preferences 128 in FIG. 1.

Process 2200 identifies locations (operation 2208). The locations are a listing of various geographical locations, venues, recreational areas, or other locations at which at least one activity can occur. The identified locations can be locations 120 in FIG. 1. The locations can be identified based on location information for the locations, such as location information 126 in FIG. 1.

Based on identified activities, aggregate activity preferences, and identified locations, process 2200 identifies a portion of employees (operation 2210) and makes a recommendation (operation 2212).

The portion of employees can be portion of employees 130 in FIG. 1. The portion of employees can be identified based on having at least one of a common desired level of wellness, a common health self-assessment data, a common health diagnostic data, or a common activity preference. Alternatively, the portion of employees can be one of a user selected subgroup employees, or an administrator selected subgroup of employees that share a common social circle, share a common department, share a common managerial level, or share a common workgroup.

The recommendation can be recommendation 132 in FIG. 1. The recommendation can include a recommended activity, such as recommended activity 136 in FIG. 1, selected from the identified activities and the aggregated activity preferences. The recommendation can include a recommended location, such as recommended location 140 in FIG. 1, selected from the identified locations. The recommendation can include a recommended time, such as recommended time 138 in FIG. 1.

Process 2200 sends the recommendation to the portion of employees (operation 2212), and terminates thereafter. The recommendation can take the form of at least one of an icon or graphic within a graphical user interface, an e-mail, a chat message, or a short messaging service (SMS) message. According to an illustrative embodiment, the recommendation can be displayed with an employee interface 146 of graphical user interface 134 in FIG. 1.

With reference next to FIG. 23, an illustration of a flowchart of a process for displaying activity preferences within a graphical user interface to achieve a desired level of wealth of wellness among employees is depicted according to an illustrative embodiment. Process 2300 may be implemented in in wellness manager 129 in wellness management system 102 in wellness management environment 100 in FIG. 1.

Process 2300 begins by identifying characteristics of the employees (operation 2302). The characteristics are tracked information about the employees that can be used to schedule activities. The characteristics can be characteristics 108 in FIG. 1.

Process 2300 identifies activities (operation 2304). The identified activities are a listing of physical activities, actions, or exercises that wellness management system 102 can recommend to employees 104 in order to achieve a desired level of wellness 112. The identified activities can be activities 110 in FIG. 1. The activities can be identified based on health factors of the activities, such as health factors 122 in FIG. 1.

Based on identified characteristics and identified activities, process 2300 determines aggregate activity preferences (operation 2306). The aggregate activity preferences can be statistical calculations, statistical weights, or other values that indicate an aggregated opinion of employees for various activities. The aggregate activity preferences can be aggregate activity preferences 128 in FIG. 1.

Process 2300 receives a selection of at least one aggregate activity preference (operation 2308). Process 2300 can receive the selection, for example, from an administrator selecting an activity type within an activity scheduling interface, such as administrator 1210 selecting one of activity types 2010 within activity scheduling interface 1800 of FIG. 18.

Process 2300 updates the graphical user interface to display selected aggregate activity preferences (operation 2310). The aggregate activity preferences can be displayed as aggregate activity preferences 2012 within activity scheduling interface 1800 of FIG. 18. Process 2300 can then iterate back to operation 2308 to receive selection of additional aggregate activity preferences.

Figure 24:
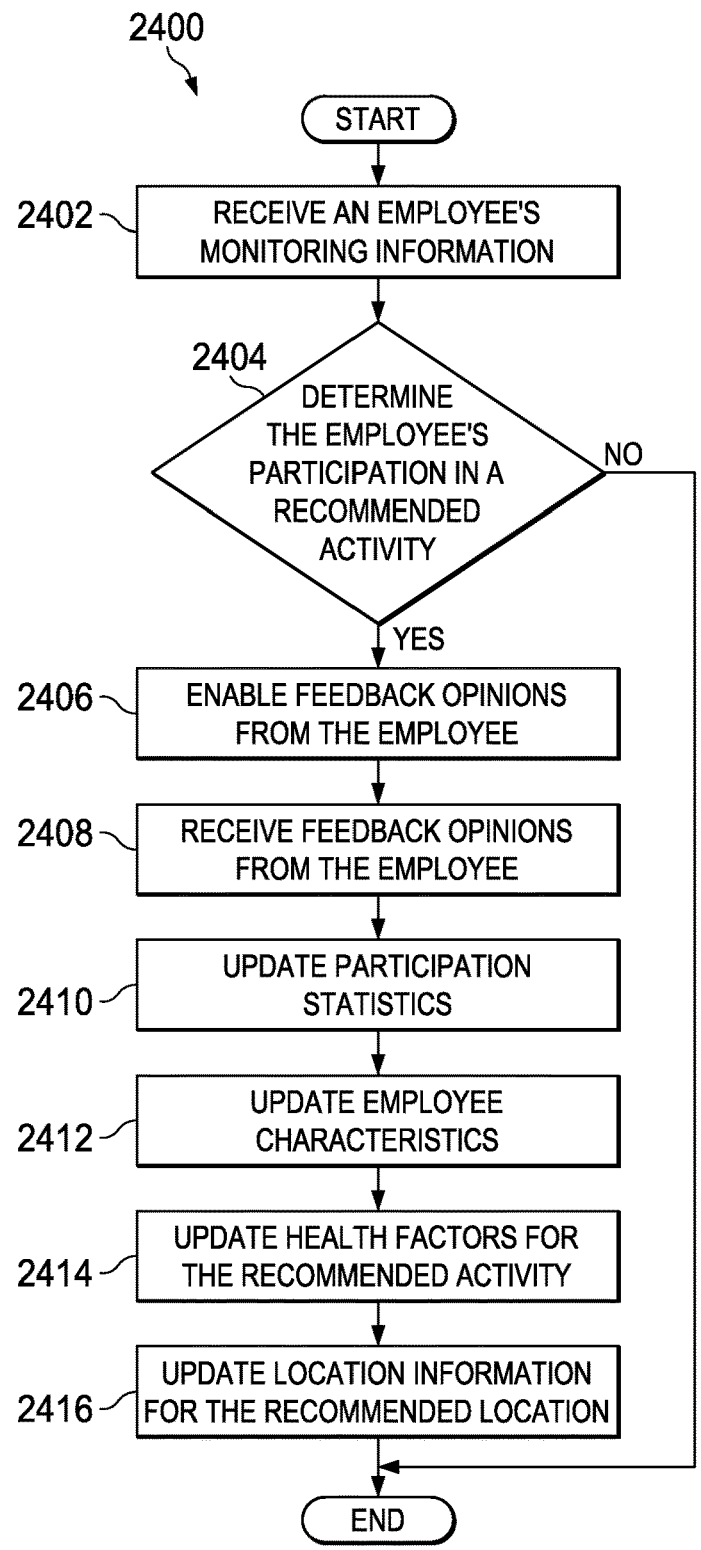
FIG. 24 is an illustration of a flowchart for of a process updating activity preferences of employees to achieve a desired level of wealth of wellness among employees depicted according to an illustrative embodiment.

With reference next to FIG. 24, an illustration of a flowchart of a process for updating activity preferences of employees to achieve a desired level of wealth of wellness among employees is depicted according to an illustrative embodiment. Process 2400 may be implemented in in wellness manager 129 in wellness management system 102 in wellness management environment 100 in FIG. 1.

Process 2400 begins by receiving an employee's monitoring information (operation 2402). Monitoring information can be monitoring information 154 of FIG. 1, and can include various fitness related metrics, such as but not limited to, at least one of a number of steps taken during a recommended activity, a number of calories burned during a recommended activity, a distance traveled during a recommended activity, an exercise duration of a recommended activity, a heart rate during a recommended activity, a respiratory rate during a recommended activity, a blood pressure during a recommended activity, or other suitable biometric data. Monitoring information can also include any employee's location. Monitoring information can also include monitored weather statistics, such as but not limited to, at least one of a measured temperature, a measured precipitation, and measured allergy conditions, such as but not limited to, at least one of measured pollen levels, measured mold levels, measured dust levels, or measured ozone levels. Process 2400 can receive monitoring information from an employee's personal fitness tracker, such as personal fitness tracker 156 in FIG. 1.

Process 2400 then determines the employee's participation in a recommend activity (operation 2404). According to one illustrative embodiment, the employee's personal fitness tracker includes a location monitoring system, such as a global positioning system. Locations of the personal fitness tracker 156 are recorded in monitoring information. Process 2400 compares recorded locations in monitoring information received from the employee's personal fitness tracker with recommended locations of recommended activities. If the location of the employee's personal fitness tracker correlates to a recommended location during a recommended time, process 2400 assumes that the employee participated in the recommended activity ("yes" at operation 2404). If it is determined that the employee did not participate in a recommend activity ("no" at operation 2404), process 2400 terminates thereafter.

Returning now to operation 2404, if it is determined that the employee did participate in a recommend activity ("yes" at operation 2404), enables feedback opinions from the employee (operation 2406). Thereafter process 2400 can receive feedback opinions from the employee (operation 2408). The feedback opinions can be, for example feedback opinions 160 in FIG. 1. The feedback opinions can include opinions about a recommended activity, such as for example but not limited to, opinions about whether the recommended activity was enjoyable to the employee, opinions about the employee's likelihood to participate in identical recommended activities, or opinions about the employee's likelihood to participate in similar recommended activities. The feedback opinions can include opinions about a recommended location, such as for example but not limited to, at least one of opinions about the weather at the recommended location during the recommended activity, opinions about a safety of the recommended location during the recommended activity, opinions about a security of the recommended location during the recommended activity, a likelihood to participate in identical recommended activities at the recommended location, or a likelihood to participate in similar recommended activities at the recommended location.

Process 2400 updates participation statistics (operation 2410). Participation statistics can be, for example participation statistics 144 in FIG. 1. Participation statistics can be updated based on monitoring information received from the employee's personal fitness tracker, such as personal fitness tracker 156, as well as the feedback opinions, such as feedback opinions 160, received from the employee using an employee interface of a graphical user interface, such as employee interface 146 of graphical user interface 134 in FIG. 1.

Process 2400 updates one or more of employee characteristics (operation 2412). The employee characteristics can be, for example, characteristics 108 in FIG. 1. Desired level of wellness 112 and health diagnostic data 116 can be updated based on monitoring information received from the employee's personal fitness tracker. Activity preferences 118 can be updated based on the feedback opinions 160 received through employee interface 146.

Process 2400 updates health factors for the recommended activity (operation 2414). The health factors can be, for example health factors 122 in FIG. 1. Health factors indicating that the recommended activity is a team activity, that the recommended activity is, that the recommended activity is an individual activity, or a popularity of the recommended activity, can be updated based on the feedback opinions 160 received through employee interface 146. Health factors indicating that the recommended activity is likely to burn a certain number of calories, or is associated with a particular intensity level can be updated based on monitoring information received from the employee's personal fitness tracker.

Process 2400 updates location information for the recommended location (operation 2416). The location information can be, for example, location information 126 in FIG. 1. Location information such as a popularity of the location, safety conditions of the location, whether the location is a recommended location, whether the location is preferred location, or whether the location carries insurance or coinsurance on a particular activity can be updated based on the feedback opinions 160 received through employee interface 146. Location information such as weather conditions and measured allergy conditions during the recommended activity can be updated based on monitoring information received from the employee's personal fitness tracker. Process 2400 terminates thereafter.

In this manner, the recommendation, scheduling, and monitoring of activities to be performed by employees as part of a health and wellness program can be made more easily as compared to currently used techniques. Because recommended activities are specifically interesting to the employee, employee participation in the health and wellness program is encouraged. As a result, employees are more likely to take advantage of activities offered by and recommended by a health and wellness program. Furthermore, by recommending, scheduling, monitoring, and analyzing activities to be performed by employees as part of a health and wellness program, a desired level of wellness among employees is enabled. These and other tasks may be performed using the visualization of health factors and activity preferences that are manipulated to interact within a graphical user interface to generate a result. As result, an operator may more efficiently perform a wellness task based on the visualization of the health factors and activity preferences in a graphical user interface.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 25:
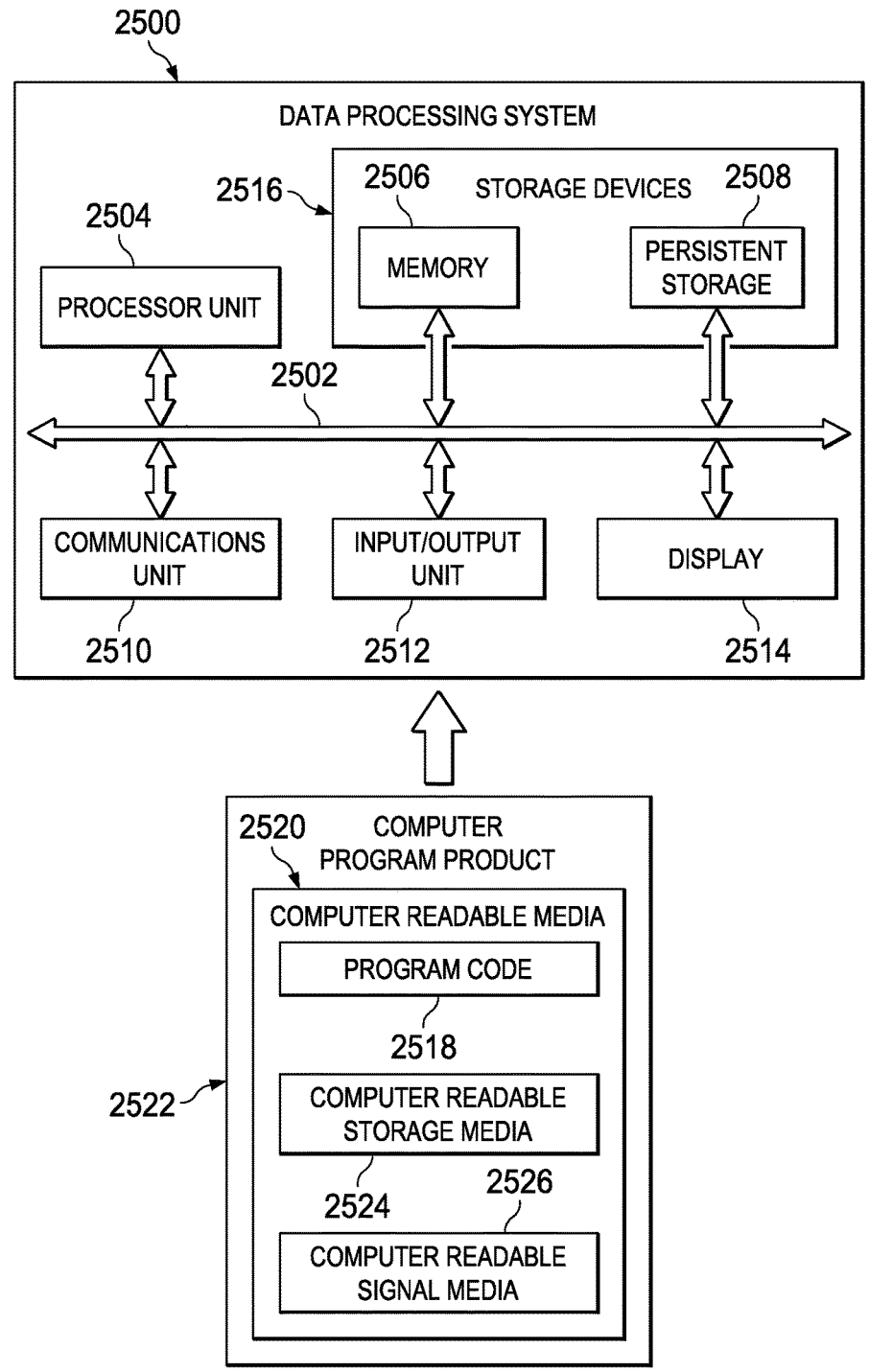
FIG. 25 is an illustration of a block diagram of a data processing system in accordance with an illustrative embodiment.

Turning now to FIG. 25, an illustration of a block diagram of a data processing system is depicted in accordance with an illustrative embodiment. Data processing system 2500 may be used to implement one or more data processing systems in wellness management system 102 in FIG. 1. In this illustrative example, data processing system 2500 includes communications framework 2502, which provides communications between processor unit 2504, memory 2506, persistent storage 2508, communications unit 2510, input/output (I/O) unit 2512, and display 2514. In this example, communication framework may take the form of a bus system.

Processor unit 2504 serves to execute instructions for software that may be loaded into memory 2506. Processor unit 2504 may be a number of processors, a multi-processor core, or some other type of processor, depending on the particular implementation.

Memory 2506 and persistent storage 2508 are examples of storage devices 2516. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 2516 may also be referred to as computer readable storage devices in these illustrative examples. Memory 2506, in these examples, may be, for example, a random access memory or any other suitable volatile or non-volatile storage device. Persistent storage 2508 may take various forms, depending on the particular implementation.

For example, persistent storage 2508 may contain one or more components or devices. For example, persistent storage 2508 may be a hard drive, a flash memory, a rewritable optical disk, a rewritable magnetic tape, or some combination of the above. The media used by persistent storage 2508 also may be removable. For example, a removable hard drive may be used for persistent storage 2508.

Communications unit 2510, in these illustrative examples, provides for communications with other data processing systems or devices. In these illustrative examples, communications unit 2510 is a network interface card.

Input/output unit 2512 allows for input and output of data with other devices that may be connected to data processing system 2500. For example, input/output unit 2512 may provide a connection for user input through at least of a keyboard, a mouse, or some other suitable input device. Further, input/output unit 2512 may send output to a printer. Display 2514 provides a mechanism to display information to a user.

Instructions for at least one of the operating system, applications, or programs may be located in storage devices 2516, which are in communication with processor unit 2504 through communications framework 2502. The processes of the different embodiments may be performed by processor unit 2504 using computer-implemented instructions, which may be located in a memory, such as memory 2506.

These instructions are referred to as program code, computer usable program code, or computer readable program code that may be read and executed by a processor in processor unit 2504. The program code in the different embodiments may be embodied on different physical or computer readable storage media, such as memory 2506 or persistent storage 2508.

Program code 2518 is located in a functional form on computer readable media 2520 that is selectively removable and may be loaded onto or transferred to data processing system 2500 for execution by processor unit 2504. Program code 2518 and computer readable media 2520 form computer program product 2522 in these illustrative examples.

In one example, computer readable media 2520 may be computer readable storage media 2524 or computer readable signal media 2526.

In these illustrative examples, computer readable storage media 2524 is a physical or tangible storage device used to store program code 2518 rather than a medium that propagates or transmits program code 2518.

Alternatively, program code 2518 may be transferred to data processing system 2500 using computer readable signal media 2526. Computer readable signal media 2526 may be, for example, a propagated data signal containing program code 2518. For example, computer readable signal media 2526 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 2500 are not meant to provide architectural limitations to the manner in which different embodiments may be implemented. The different illustrative embodiments may be implemented in a data processing system including components in addition to or in place of those illustrated for data processing system 2500. Other components shown in FIG. 25 can be varied from the illustrative examples shown. The different embodiments may be implemented using any hardware device or system capable of running program code 2518.

Thus, the illustrative embodiments provide a method and apparatus for managing wellness of employees. In one illustrative example, an employee management wellness system receives a group of health factors for activities and group of preferences for activities of the employees. The wellness system identifies a recommendation for an activity for a portion of the employees based on the group health factors, the group of preferences, and information for locations where recommended activities are to occur. The wellness system then sends the recommendation for the activity to the portion of the employees.

In this manner, the recommendation, scheduling, and monitoring of activities to be performed by employees as part of a health and wellness program can be made more easily as compared to currently used techniques. Because recommended activities are specifically interesting to the employee, employee participation in the health and wellness program is encouraged. As a result, employees are more likely to take advantage of activities offered by and recommended by a health and wellness program. Furthermore, by recommending, scheduling, monitoring, and analyzing activities to be performed by employees as part of a health and wellness program, a desired level of wellness among employees is enabled.

The description of the different illustrative embodiments has been presented for purposes of illustration and description, and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component. In particular, wellness manager is configured to perform the different operations described as well as other operations using at least one of program code, hardware, firmware, or other suitable components.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method, comprising:
   receiving, by a computer system, a group of health factors and a group of preferences for activities of a plurality of employees, the group of preferences including preferences for activity locations;
   scheduling, by the computer system, a recommended activity in the activities based on the group of health factors and the group of preferences;
   generating, by the computer system, a recommendation for the recommended activity for a portion of the plurality of employees based on the group of health factors, the group of preferences, and information for a location where the recommended activity is to occur;
   sending, by the computer system, the recommendation for the recommended activity to the portion of the plurality of employees; and
   determining, by the computer system, when a first employee of the portion of the plurality of employees performs the recommended activity, wherein the recommendation that results in the recommended activity being performed by the employee contributes to a desired level of wellness for the first employee.

2. The method of claim 1, wherein the information for the location comprises a popularity for the location where the recommended activity is to occur, expected weather conditions for the location where the recommended activity is to occur, safety conditions for the location where the recommended activity is to occur, whether the location is a recommended location, and whether the location carries insurance for the recommended activity.

3. The method of claim 1, wherein generating the recommendation comprises:
   correlating, by the computer system, the recommendation for the recommended activity to a plurality of scheduled availabilities of the portion of the employees, wherein the plurality of scheduled availabilities indicate when the first employee is available to participate in the recommended activity based on scheduled vacation days for the portion of the employees, sick days for the portion of the employees, and a scheduled location of the portion of the employees during a recommended time for the recommended activity; and
   wherein sending the recommendation comprises sending, by the computer system, the recommendation for the recommended activity to only the portion of the employees that is available to participate in the recommended activity as indicated by the plurality of scheduled availabilities for the portion of the employees.

4. The method of claim 1, wherein determining when the first employee performs the recommended activity further comprises:

receiving, by the computer system, monitoring information from a personal fitness tracker associated with the first employee;
determining, by the computer system, whether location information of the first employee during a recommended time for the recommended activity matches a first location for the recommended activity; and
responsive to determining that the location information of the first employee during the recommended time for the recommended activity matches the first location for the recommended activity, correlating, by the computer system, the monitoring information with the recommended activity.

5. The method of claim 4, wherein monitoring further comprises:
determining, by the computer system, when the portion of the employees performs the recommended activity; and
receiving, by the computer system, data from a set of personal fitness trackers, wherein the set of personal fitness trackers are heterogeneous personal fitness trackers.

6. The method of claim 4, wherein the monitoring information comprises the location information of the first employee during the recommended activity, weather conditions during the recommended activity, biometric data of the first employee during the recommended activity, and a number of calories burned by the first employee during the recommended activity.

7. The method of claim 5, further comprising updating, by the computer system and responsive to correlating the monitoring information to the recommended activity, the group of preferences for the portion of the employees having the location information during the recommended time for the recommended activity that matches the first location for the recommended activity.

8. The method of claim 4, further comprising:
receiving, by the computer system, feedback opinions for the recommended activity from the first employee having the location information during the recommended time for the recommended activity that matches the first location for the recommended activity, wherein the feedback opinions comprise information regarding at least one of weather at the first location during the recommended activity, safety of the first location during the recommended activity, security of the first location during the recommended activity, whether the recommended activity was enjoyable to the first employee, whether the first location was enjoyable to the first employee, a first likelihood of the first employee to participate in the recommended activity, a second likelihood of the first employee to participate in similar ones of the recommended activity, or a third likelihood of the first employee to participate in other ones of the recommended activity at the first location.

9. The method of claim 8, wherein the recommended activity is a first activity, and further comprising generating, by the computer system, a second recommendation for a second recommended activity for the first employee, the second recommendation based on the feedback opinions received from the first employee having the location information during the recommended time for the recommended activity that matches the first location for the recommended activity.

10. The method of claim 1, wherein:
the group of health factors comprises a projected number of calories burned during the activities, a physical intensity level of the activities, and a level of social interaction during the activities; and
the group of preferences comprises a desired number of calories to be burned during the activities, a desired physical intensity level of the activities, and a desired level of social interaction.

11. The method of claim 1, wherein generating the recommendation further comprises:
generating, by the computer system, the recommendation for the recommended activity based on:
health self-assessment data for the portion of the plurality of employees; and
health diagnostic data for the portion of the plurality of employees, the health diagnostic data different than the health self-assessment data; and
wherein the health self-assessment data comprises employee self-evaluation of at least one of health, nutrition, stress, tobacco use, alcohol use, or sleep habits, and the health diagnostic data comprises measurement of at least one of blood pressure, cholesterol, triglycerides, glucose, or body mass index.

12. The method of claim 1, wherein generating the recommendation further comprises:
identifying, by the computer system, a lower cost for at least one of health insurance or health care resulting from the portion of the plurality of employees performing the recommended activity; and
displaying, by the computer system, the lower cost to the portion of the plurality of employees as an incentive for the portion of the plurality of employees to perform the recommended activity in the recommendation.

13. A system comprising:
a display system; and
a wellness management system implemented with a computer system, the computer system in communication with the display system, wherein the wellness management system is configured to:
receive a group of health factors and a group of preferences for activities of a plurality of employees, the group of preferences comprising a first preference for activity locations;
schedule a recommended activity in the activities based on the group of health factors and the group of preferences;
generate a recommendation for the recommended activity for a portion of the plurality of employees based on the group of health factors, the group of preferences, and information for locations where recommended activities are to occur;
send the recommendation for the recommended activity to the portion of the plurality of employees; and
determine when a first employee of the plurality of employees performs the recommended activity.

14. The computer system of claim 13, wherein the information for locations comprises a popularity for the locations, expected weather conditions for the locations, safety conditions for the locations, whether any of the locations are a recommended location, and whether any of the locations carry insurance on the recommended activity.

15. The computer system of claim 13, wherein the wellness management system is further configured to:
in generating the recommendation, correlate, the recommendation to schedules for the portion of the employees, wherein the schedules indicate when the first employee is available to participate in the recommended activity, based on at least one of scheduled vacation days for the portion of the employees, sick days for the portion of the employees, or a scheduled location of the portion of the employees during a recommended time for the recommended activity; and in sending the recommendation, send the recommendation to only the portion of the employees that is available to participate in the recommended activity as indicated by the schedules for the portion of the employees.

16. The computer system of claim 13, wherein the wellness management system, in determining when the first employee performs the recommended activity, is further configured to:

receive monitoring information from a personal fitness tracker associated with the first employee;

determine whether location information of the first employee during a recommended time for the recommended activity matches a location for the recommended activity; and responsive to determining that the location information of the first employee during the recommended time for the recommended activity matches the location for the recommended activity, correlate the monitoring information with the recommended activity.

17. The computer system of claim 16, wherein the wellness management system, in determining when the first employee performs the recommended activity, is further configured to:

determine when the portion of the employees perform the recommended activity; and receive data from a set of personal fitness trackers, wherein the set of personal fitness trackers are heterogeneous personal fitness trackers.

18. The computer system of claim 16, wherein the monitoring information comprises the location information of the first employee during the recommended activity, weather conditions during the recommended activity, biometric data of the first employee during the recommended activity, and a number of calories burned by the first employee during the recommended activity.

19. The computer system of claim 17, wherein the wellness management system is further configured to, responsive to correlating the monitoring information to the recommended activity, update the group of preferences for the portion of the employees having the location information during the recommended time for the recommended activity that matches the location for the recommended activity.

20. The computer system of claim 16, wherein the wellness management system is further configured to receive feedback opinions about the recommended activity from the first employee having the location information during the recommended time for the recommended activity that matches the location for the recommended activity, wherein the feedback opinions comprise information regarding at least one of weather at the location during the recommended activity, safety of the location during the recommended activity, security of the location during the recommended activity, whether the recommended activity was enjoyable to the first employee, whether the location was enjoyable to the first employee, a first likelihood of the first employee to participate in the recommended activity, a second likelihood of the first employee to participate in similar ones of recommended activities, or a third likelihood of the first employee to participate in other ones of recommended activities at the location.

21. The computer system of claim 19, wherein the recommended activity is a first activity, and the wellness management system is further configured to generate a second recommendation for a second recommended activity for the first employee, the second recommendation based on feedback opinions received from the first employee having the location information during the recommended time for the recommended activity that matches the location for the recommended activity.

22. The computer system of claim 13, wherein:

the group of health factors for the activities comprises a projected number of calories burned during the activities, a physical intensity level of the activities, and a level of social interaction during the activities; and the group of preferences further comprises a desired number of calories to be burned during the activities, a desired physical intensity level of the activities, and a second preference for social interaction during the activities.

23. The computer system of claim 13, wherein the wellness management system, in generating the recommendation, is further configured to generate the recommendation for the recommended activity based on health self-assessment data and health diagnostic data for the portion of the employees, wherein the health self-assessment data comprises employee self-evaluation of at least one of health, nutrition, stress, tobacco use, alcohol use, or sleep habits, and wherein the health diagnostic data comprises measurement of at least one of blood pressure, cholesterol, triglycerides, glucose, or body mass index.

24. The computer system of claim 13, wherein the wellness management system, in generating the recommendation, is further configured to:

identify a lower cost for at least one of health insurance or health care resulting from the portion of the employees performing the recommendation; and display the lower cost to the portion of the employees as an incentive for the portion of the employees to perform the recommendation.

25. A computer program product, comprising:

a computer readable storage media;

first program code, stored on the computer readable storage media, for receiving a group of health factors for activities and a group of preferences for the activities for a plurality of employees;

second program code, stored on the computer readable storage media, for generating a recommendation for a recommended activity in the activities for a portion of the plurality of employees based on the group of health factors, the group of preferences, and information for a plurality of locations, the information for the plurality of locations comprising a first location for the recommended activity, and insurance coverage for the recommended activity at the first location;

third program code, stored on the computer readable storage media, for scheduling the recommended activity based on the group of health factors and the group of preferences;

fourth program code, stored on the computer readable storage media, for sending the recommendation for the recommended activity to the portion of the plurality of employees; and fifth program code, stored on the computer readable storage media, for monitoring when a first employee performs the recommended activity, wherein recommendations that result in the recommended activity being performed by any of the portion of the plurality of employees contribute to a desired level of wellness.

26. The computer program product of claim 25, wherein the information for the plurality of locations further comprises at least one of a popularity for the locations, expected weather conditions for the locations, safety conditions for the locations, or whether the first location is a recommended location.

27. The computer program product of claim 25, wherein the second program code further comprises:
sixth program code, stored on the computer readable storage media, for correlating the recommendation to at least one of a plurality of time availabilities for the portion of the plurality of employees, wherein the at least one of the plurality of time availabilities indicate when the first employee is available to participate in the recommended activity, based on scheduled vacation days for the portion of the plurality of employees, sick days for the portion of the plurality of employees, or a scheduled location of the portion of the plurality of employees during a recommended time for the recommended activity; and
wherein the fourth program code further comprises seventh program code, stored on the computer readable storage media, for sending the recommendation to only the portion of the plurality of employees that is available to participate in the recommended activity as indicated by the at least one of the plurality of time availabilities for the portion of the plurality of employees.

28. The computer program product of claim 25, wherein the fifth program code further comprises:
sixth program code, stored on the computer readable storage media, for receiving monitoring information from a personal fitness tracker associated with the first employee;
seventh program code, stored on the computer readable storage media, for determining whether location information of the first employee during a recommended time for the recommended activity matches the first location for the recommended activity; and
eighth program code, stored on the computer readable storage media, for correlating the monitoring information with the recommended activity in response to determining that the location information of the first employee during the recommended time for the recommended activity matches the first location for the recommended activity.

29. The computer program product of claim 28, wherein the fifth program code further comprises:
ninth program code, stored on the computer readable storage media, for determining when the portion of the plurality of employees perform the recommended activity; and
tenth program code, stored on the computer readable storage media, for receiving data from a set of personal fitness trackers, wherein the set of personal fitness trackers are heterogeneous personal fitness trackers.

30. The computer program product of claim 28, wherein the monitoring information comprises the location information of the first employee during the recommended activity, weather conditions during the recommended activity, biometric data of the first employee during the recommended activity, and a number of calories burned by the first employee during the recommended activity.

31. The computer program product of claim 29, further comprising eleventh program code, stored on the computer readable storage media, for updating the group of preferences for the portion of the plurality of employees having the location information during the recommended time for the recommended activity that matches the first location for the recommended activity responsive to correlating the monitoring information to the recommended activity.

32. The computer program product of claim 25, further comprising:
sixth program code, stored on the computer readable storage media, for receiving feedback opinions from the first employee, the first employee having location information during a recommended time for the recommended activity that matches the first location for the recommended activity, the feedback opinions comprising information for at least one of weather at the first location during the recommended activity, safety of the first location during the recommended activity, security of the first location during the recommended activity, whether the recommended activity was enjoyable to the first employee, whether the first location was enjoyable to the first employee, a first likelihood of the first employee to participate in the recommended activity, a second likelihood of the first employee to participate in similar ones of recommended activities, or a third likelihood of the first employee to participate in other ones of recommended activities at the first location.

33. The computer program product of claim 32, wherein the recommended activity is a first activity, the computer program product further comprising seventh program code, stored on the computer readable storage media, for generating a second recommendation for a second recommended activity for the first employee, the second recommendation based on the feedback opinions received from the first employee.

34. The computer program product of claim 25, wherein:
the group of health factors for the activities comprises a projected number of calories burned during the activities, a physical intensity level of the activities, and a level of social interaction during the activities; and
the group of preferences comprises a desired number of calories to be burned during the activities, a desired physical intensity level of the activities, a first preference for activity locations, and a second preference for social interaction.

35. The computer program product of claim 25, wherein the second program code further comprises sixth program code, stored on the computer readable storage media, for generating the recommendation, wherein the recommendation is further based on at least one of:
health self-assessment data for the portion of the plurality of employees; or
health diagnostic data for the portion of the plurality of employees; and
wherein the health self-assessment data comprises employee self-evaluation of at least one of health, nutrition, stress, tobacco use, alcohol use, or sleep habits, and the health diagnostic data comprises measurement of at least one of blood pressure, cholesterol, triglycerides, glucose, or body mass index.

36. The computer program product of claim 25, wherein the second program code further comprises:
sixth program code, stored on the computer readable storage media, identifying a lower cost for at least one of health insurance or health care resulting from the portion of the plurality of employees performing the recommendation; and
seventh program code, stored on the computer readable storage media, for displaying the lower cost to the portion of the plurality of employees as an incentive for the portion of the plurality of employees to perform the recommendation.

\* \* \* \* \*